United States Patent
Zimmers et al.

(10) Patent No.: US 10,363,141 B2
(45) Date of Patent: Jul. 30, 2019

(54) ARTIFICIAL DISC

(71) Applicant: AxioMed Spine Corp., Garfield Hts., OH (US)

(72) Inventors: Kari Zimmers, Solon, OH (US); Keith Duke, Cleveland, OH (US); James Kuras, Macedonia, OH (US); Rebecca Blice, Akron, OH (US); J. Edward Barber, Avon, OH (US); Tawny Brag, Chicago, IL (US)

(73) Assignee: AXIOMED, LLC, Malden, MA (US)

( * ) Notice: Subject to any disclaimer, the term of this patent is extended or adjusted under 35 U.S.C. 154(b) by 501 days.

(21) Appl. No.: 14/215,340

(22) Filed: Mar. 17, 2014

(65) Prior Publication Data

US 2014/0316524 A1 Oct. 23, 2014

Related U.S. Application Data

(60) Provisional application No. 61/792,057, filed on Mar. 15, 2013.

(51) Int. Cl.
*A61F 2/44* (2006.01)
*A61F 2/30* (2006.01)

(52) U.S. Cl.
CPC .......... *A61F 2/442* (2013.01); *A61F 2/30771* (2013.01); *A61F 2002/30367* (2013.01); *A61F 2002/30563* (2013.01); *A61F 2002/30784* (2013.01); *A61F 2002/30841* (2013.01)

(58) Field of Classification Search
CPC ............ A61F 2/442; A61F 2002/30367; A61F 2002/30563; A61F 2002/30784; A61F 2002/30841; A61F 2002/30771
USPC .......................................... 623/17.11–17.16
See application file for complete search history.

(56) References Cited

U.S. PATENT DOCUMENTS

| | | | | |
|---|---|---|---|---|
| 3,867,728 A * | 2/1975 | Stubstad | .................. | A61F 2/441 128/DIG. 21 |
| 4,839,215 A * | 6/1989 | Starling | ............... | A61C 8/0012 428/131 |
| 2004/0054411 A1* | 3/2004 | Kelly | ..................... | A61B 17/02 623/17.13 |
| 2006/0173542 A1* | 8/2006 | Shikinami | ........... | A61F 2/30965 623/14.12 |
| 2006/0259144 A1* | 11/2006 | Trieu | ...................... | A61F 2/442 623/17.13 |
| 2011/0144417 A1* | 6/2011 | Jagger | .................... | A61F 2/0045 600/30 |

* cited by examiner

*Primary Examiner* — Zade Coley
*Assistant Examiner* — Jessica Weiss
(74) *Attorney, Agent, or Firm* — AKC Patents, LLC; Aliki K. Collins

(57) ABSTRACT

An artificial disc to replace a damaged spinal disc in a spinal column includes a resilient core which is fixedly connected to first and second plates. The first and second plates engage upper and lower vertebra in the patient's spine. The inner side of at least one of the first and second plates has an array of recesses into which said resilient core extends. The array of recesses includes a plurality of recesses. Each of the recesses of the plurality of recesses has surfaces which are integrally formed as one piece with the plate.

13 Claims, 14 Drawing Sheets

ARTIFICIAL DISC

RELATED APPLICATION

This application claims the benefit of U.S. Provisional Application Ser. No. 61/792,057 filed Mar. 15, 2013 the subject matter of which is hereby incorporated herein by reference in their entirety.

FIELD OF INVENTION

The present invention relates to an artificial disc to replace a damaged spinal disc in a patient's spinal column.

BACKGROUND OF THE INVENTION

Known artificial discs which are utilized to replace damaged spinal discs in a patient's spinal column include a resilient core which is disposed between upper and lower plates. The upper plate has an upper side surface which engages an upper vertebra in a patient's spinal column. A lower plate has a lower side surface which engages a lower vertebra in the patient's spinal column. The mechanical function of the artificial disc is based on the size (both in volume and cross-sectional thickness) of the resilient core which is incorporated in the artificial disc. The size and geometry of the core which is included in the artificial disc, dictates how closely the design can replicate the natural characteristics of the disc which it replaces.

Known artificial discs which are utilized to replace a damaged spinal disc in a patient's spinal column are disclosed in U.S. Pat. Nos. 5,534,030; 6,607,558; and 7,169,181. In addition, an artificial disc is disclosed in U.S. Patent Publication No. 2008/0306609.

SUMMARY OF THE INVENTION

An improved artificial disc is utilized to replace a damaged spinal disc in a spinal column. The artificial disc includes a resilient core which is disposed between first and second plates. The first plate has an outer side surface which is engageable with a first vertebra of the spinal column and an inner side. The second plate has an outer side which is engageable with a second vertebra of the spinal column and an inner side.

In accordance with one of the features of the invention, the inner side of at least one of the plates has an array of recesses. The array of recesses includes a plurality of recesses. Each of the recesses of the plurality of recesses has surfaces which are integrally formed as one piece with the one plate of the first and second plates.

If desired, the inner side of the other plate may also be provided with an array of recesses which may be formed in the same general matter and have the same general configuration as the recesses formed in the one plate. If desired, each of the recesses of the plurality of recesses in either one of the plates may have a rim portion formed by a polygonal array of interconnected rim sections.

Also, each of the recesses of the plurality of recesses may extend in at least one row. The plurality of recesses may extend in a plurality of rows that may extend generally parallel to each other. The arcuate surfaces defining the recesses in a first row of recesses may form an undulating wave having an amplitude greater than an amplitude of an undulating wave formed by arcuate surfaces in a second row of recesses.

Furthermore, the plurality of recesses may include at least first and second concentric recesses. The concentric recesses may be at least partially defined by arcuate surfaces extending between the concentric recesses. The plurality of recesses may include at least one recess extending generally transverse to the concentric recesses. The at least one recess extending generally transverse to the concentric recesses may extend generally perpendicular to the concentric recesses. Also, the at least one recess extending transverse to the concentric recesses may have a first semi-circular shaped longitudinal end and a second semi-circular shaped longitudinal end. At least one of the first and second semi-circular shaped longitudinal ends may be defined by a generally convex arcuate surface extending from a bottom of one of the concentric recesses to a concave arcuate surface extending from the convex arcuate surface to a bottom of the at least one recess extending transverse to the concentric recesses.

The present invention has a plurality of features. These features may be used separately or may be used together as disclosed herein. One or more of the features of the invention may be used with features from the prior art.

BRIEF DESCRIPTION OF THE DRAWINGS

The foregoing and other features of the present invention will become apparent to one skilled in the art to which the present invention relates upon consideration of the following description of the invention with reference to the accompanying drawings in which.

DESCRIPTION OF THE INVENTION

General Description

Figure 1:
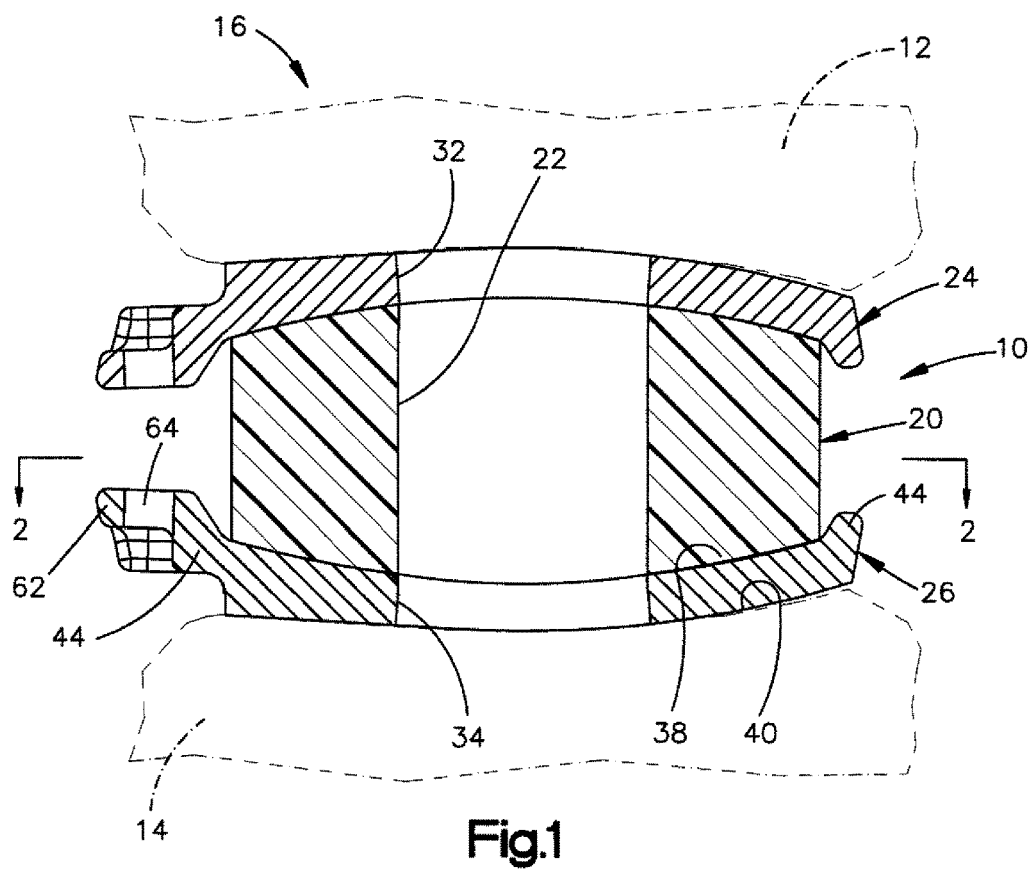
FIG. 1 is a simplified fragmentary schematic sectional view of an artificial disc constructed in accordance with the present invention and disposed in a patient's spinal column.

The present invention relates to an artificial disc 10 (FIG. 1) which replaces a damaged or degenerated disc in a spinal column of a human patient. The artificial disc 10 is disposed between upper and lower vertebrae 12 and 14 of a human spinal column 16. Although the artificial disc 10 is particularly advantageous for replacement of a damaged spinal disc in a cervical portion of the spinal column 16, the artificial disc may be utilized to replace a damaged disc in the lumbar portion of a patient's spinal column.

The artificial disc 10 includes a resilient core or central section 20 formed of a polymeric material. The resilient core 20 is made of a urethane silicon blend. However, it is contemplated that the resilient core 20 may be formed of different materials if desired. The illustrated core 20 has a cylindrical central opening or passage 22. However, it is contemplated that the passage 22 may have any desired shape and not extend through the core 20 so that it defines a recess. It is also contemplated that the passage 22 could be eliminated and the core 20 formed of a solid piece of material which is free of openings which extend between axially opposite sides of the core.

Upper and lower plates 24 and 26 are fixedly connected to opposite sides of the core 20. The upper and lower plates 24 and 26 are prevented from sliding or moving relative to upper and lower surfaces of the core 20. The upper and lower plates 24 and 26 are formed of metal, specifically titanium. However, the upper and lower plates 24 and 26 may be formed of other biocompatible materials. For example, the upper and lower plates 24 and 26 may be formed of a polymeric material.

The upper plate 24 engages the upper vertebra 12. Similarly, the lower plate 26 engages the lower vertebra 14. Although the upper and lower plates 24 and 26 have the same construction, they may have different constructions if desired.

It is contemplated that the upper and lower plates 24 and 26 may be provided with features to resist expulsion of the artificial disc from between the upper and lower vertebrae 12 and 14. The features which resist expulsion of the artificial disc 10 from between the upper and lower vertebrae 12 and 14 may be teeth, fins or ridges. The features which resist expulsion of the artificial disc 10 from between the vertebrae 12 and 14 may be integrally formed as one piece with the upper and lower plates 24 and 26. Alternatively, the features which resist expulsion of the artificial disc 10 from between the vertebrae 12 and 14 may be formed separately from the upper and lower plates 24 and 26 and connected to the upper and lower plates. Illustrative examples of some of the many features which may be used to resist expulsion of the artificial disc 10 from between the upper and lower vertebrae 12 and 14 are illustrated in U.S. Pat. Nos. 5,534,030; 6,607,558; and 7,128,761.

The identical upper and lower plates 24 and 26 are domed or bowed to fit the upper and lower vertebrae 12 and 14 to further resist expulsion. However, the upper and lower plates 24 and 26 may have a generally flat construction. If desired, the upper and lower plates 24 and 26 may have a coating or surface treatment on the bone-interface side to promote bony ingrowth into the plates.

The illustrated upper and lower plates 24 and 26 have circular central openings 32 and 34 (FIG. 1) which are axially aligned with the cylindrical opening or passage 22 through the resilient core 20. If desired, the openings 32 and 34 in the upper and lower plates 24 and 26 may be omitted or may receive members to close the openings. Alternatively, the openings 32 and 34 in the upper and lower plates 24 and 26 may have a configuration other than the illustrated circular configuration. Similarly, the cylindrical opening 22 through the resilient core 20 may be eliminated or may have a configuration other than the illustrated cylindrical configuration.

Figure 2:
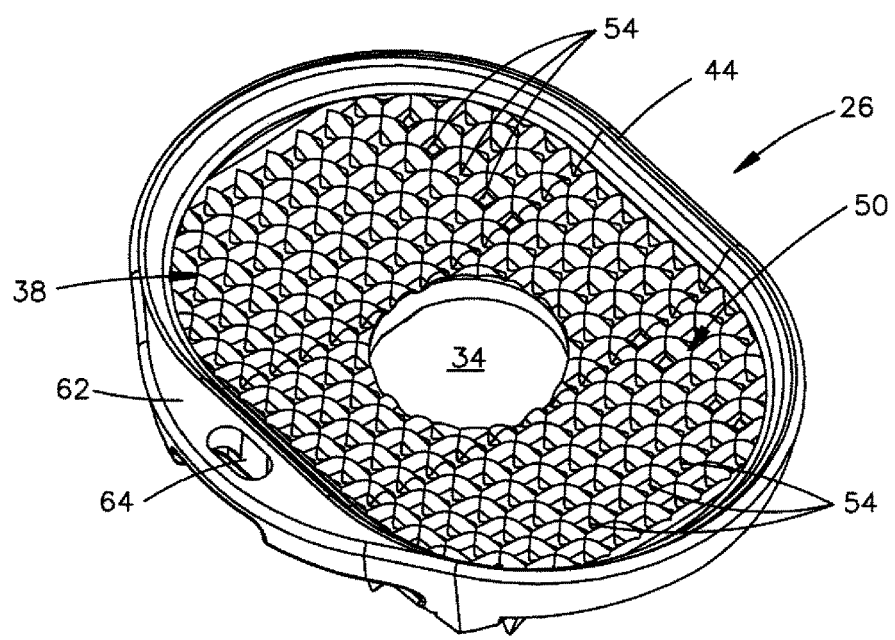
FIG. 2 is a schematic pictorial illustration, taken generally along the line 2-2 of FIG. 1, illustrating a lower plate of the artificial disc of FIG. 1.

The lower plate 26 has a generally oval configuration (FIG. 2). Inner and outer sides 38 and 40 are domed or bowed to fit the anatomy of the lower vertebrae 14 and to resist expulsion of the artificial disc 10 from between the upper and lower vertebrae 12 and 14 (FIG. 1). The inner and outer sides 38 and 40 of the lower plate 26 have the same center of curvature. However, the center of curvature of the inner side 38 may, if desired, be offset from the center of curvature of the outer side 40.

A peripheral rim or flange 44 is provided on the lower plate 26 (FIG. 2) to restrict transverse or sideways deflection of the resilient core 20. If desired, the peripheral rim 44 may be omitted. Although only the lower plate 26 is illustrated in FIG. 2, it should be understood that the upper plate 24 (FIG. 1) is identical to the lower plate 26. Although the upper and lower plates 24 and 26 have the same construction, they may have different constructions if desired.

In accordance with one of the features of the present invention, the inner side 38 (FIG. 2) of the lower plate 26 is provided with an array 50 of recesses. The array 50 of recesses includes a plurality 54 of recesses. Each of the recesses 56 (FIG. 3) in the plurality 54 of recesses has the same configuration. In the embodiment of the invention illustrated in FIGS. 1-3, each of the recesses in the array 50 of recesses has the same configuration. However, it is contemplated that some of the recesses in the array 50 may have a configuration which is different than the configuration of other recesses in the array.

The polymeric material of the resilient core 20 is fixedly bonded to the inner side 38 of the lower plate 26. This bonding may be effected by molding the core to the plates 26. It is contemplated that the bonding may be effected by heating or otherwise softening the material on the lower side of the resilient core 20 and pressing the lower side of the resilient core firmly against the inner side 38 of the lower plate 26. If desired, an adhesive may be used to fixedly interconnect the resilient core 20 and the inner side 38 of the lower plate 26.

The polymeric material of the resilient core flows into each of the recesses 56 in the array 50 of recesses. The array 50 of recesses is effective to increase the surface area of contact between the lower side (as viewed in FIG. 1) of the resilient core 20 and the lower plate 26. The surfaces of the recesses 56 in the array 50 of recesses are integrally formed as one piece with the lower plate 26. The recesses in the array 50 of recesses prevent relative movement between the resilient core 20 and the lower plate 26 at the interface between the core and lower plate. The resilient core 20 and upper plate 24 are fixedly interconnected in the same manner as are the resilient core and lower plate 26.

The recesses in the array 50 of recesses provide mechanical features akin to a dam and help to mechanically lock the polymeric material of the resilient core 20 to the lower plate 26. By having the polymeric material of the resilient core 20 move into the recesses 56 in the array 50 of recesses, the surface area engaged by the resilient core tends to be maximized to promote rotational stability along the polymer-to-metal interface between the resilient core 20 and the lower plate 26. Movement of the resilient material of the core 20 into the recesses 56 in the array 50 of recesses may be achieved under the influence of pressure applied against the core.

Adhesive may be provided between the material of the resilient core 20 and the lower plate 26. If the polymeric material of the resilient core 20 is softened and subsequently solidified, a secure bond is obtained to fixedly interconnect the resilient core and the lower plate 26 without using an adhesive. If desired, the surfaces of the recesses in the array 50 of recesses may be etched to further promote mechanical bonding with the resilient core 20. Of course, an adhesive may be utilized in conjunction with softening of the material of the resilient core 20.

Figure 3:
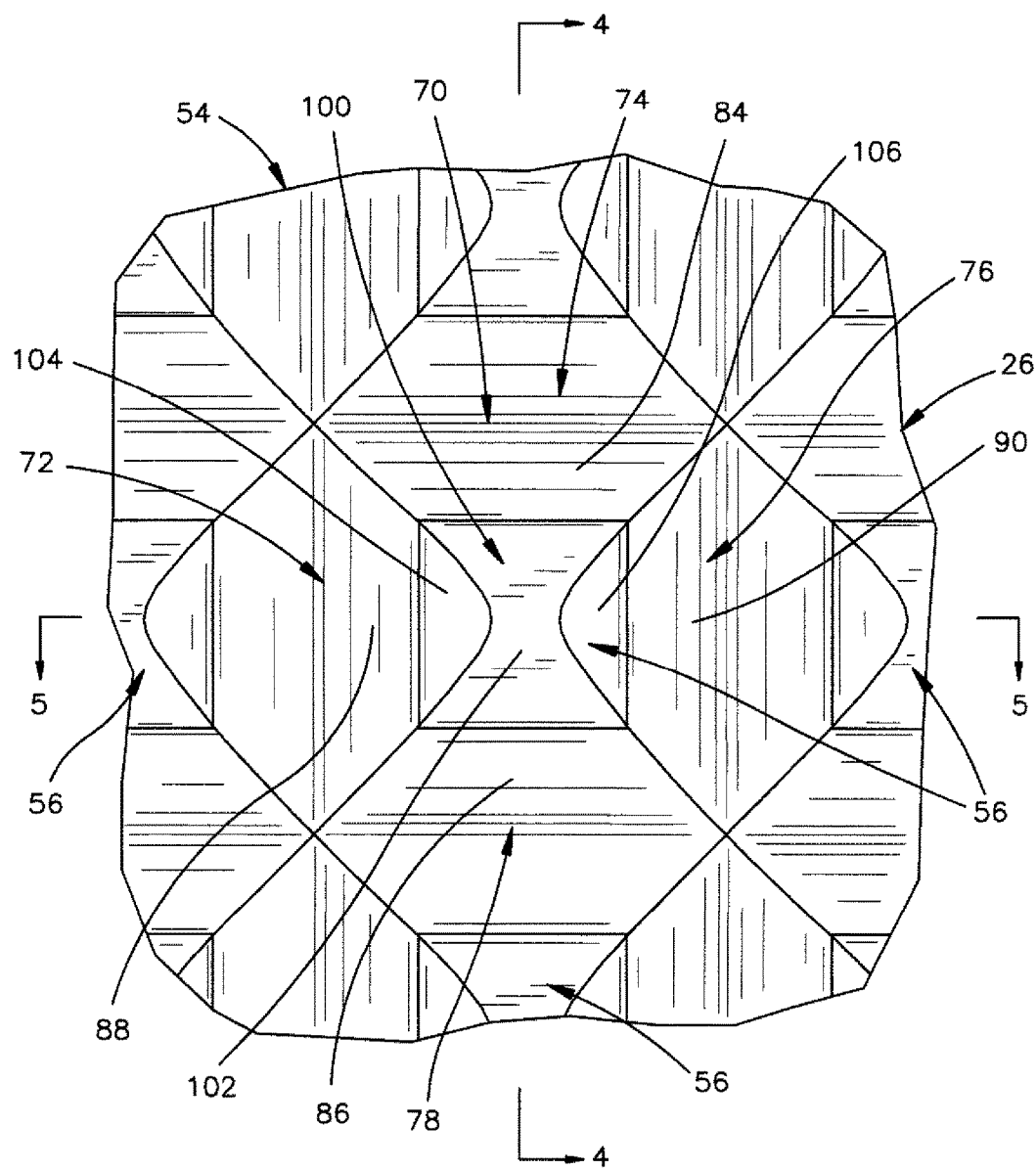
FIG. 3 is an enlarged schematic illustration of recesses which form part of an array of recesses formed in the lower plate of the artificial disc of FIG. 1.

Although only the lower plate 26 has been illustrated in FIGS. 2 and 3, it should be understood that the upper plate 24 is identical to the lower plate 26. Thus, both of the plates 24 and 26 are formed of metal, specifically, titanium, and have inner sides, corresponding to the inner side 38 of the lower plate 26, in which an array of recesses, corresponding to the array 50 of FIG. 2, is formed. The upper plate 24 is fixedly bonded to the upper (as viewed in FIG. 1) side of the resilient core 20 in the same manner as in which the lower plate 26 is fixedly bonded to the resilient core. If desired, the upper and lower plates 24 and 26 may not be identical and may have substantially different constructions.

To facilitate positioning of the artificial disc 10 between the upper and lower vertebrae, a flange 62 is connected with the peripheral rim 44 of the lower plate 26. An opening 64 is provided in the flange 62 for engagement by an insertion tool. Similarly, the upper plate 24 is provided with a flange, corresponding to the flange 62, and having an opening for engagement with the insertion tool. The insertion tool has the same construction as is disclosed in U.S. Pat. No. 7,128,761. However, it should be understood that insertion tools having a different construction may be utilized to insert the artificial disc 10 between the upper and lower vertebrae 12 and 14.

Since the array 50 of recesses in the lower plate 26 and the corresponding array of recesses in the upper plate 24 are integrally formed by surfaces of the upper and lower plates 24 and 26, the size of the resilient core can be maximized by minimizing the thickness of the upper and lower plates 24 and 26. The greater the size of the resilient core 20 and the amount of polymer disposed in the resilient core, the more closely the design of the artificial disc 10 can replicate human disc characteristics, such as stiffness. Therefore, for a given space between upper and lower vertebrae 12 and 14, the thickness of the resilient core 20 is maximized while the thickness of the upper and lower plates 24 and 26 is minimized.

The thickness of the resilient core 20, that is the height of the resilient core 20 along the central axis of a patient's spinal column 16, is maximized. The thicknesses or heights of the upper plate 24 and lower plate 26 along the central axis of the patient's spinal column 16 is minimized. Although it is believed that this construction of the artificial disc 10 may be found to be particularly advantageous for use in the cervical portion of a patient's spine, an artificial disc having this construction may be utilized in the lumbar portion of the patient's spine.

It has previously been suggested that porous coatings which are formed of sintered beads be provided on plates, corresponding to the upper and lower plates 24 and 26, of an artificial disc. A porous coating, such as a sintered bead coating, requires a minimum plate thickness of at least two millimeters (2 mm). The upper and lower plates 24 and 26 have a plate thickness of one millimeter (1 mm), exclusive of the peripheral rim 44. The recesses 56 have a depth (vertical extent) of 0.50 millimeter. Due to the plate thickness required for a sintered bead or porous coating, it is believed that a beaded surface may be disadvantageous when trying to maximize the amount of polymer in the resilient core 20. However, if desired, a porous coating formed by sintered beads or other materials may be provided on the upper and/or lower plates 24 and 26. It is contemplated that the upper and/or lower plates 24 and 26 and the recesses 56 may have dimensions other than the aforementioned dimensions.

Recess Configuration

The recesses 56 of the plurality 54 of recesses (FIG. 3) all have the same configuration. In the embodiment of the invention illustrated in FIGS. 2 and 3, all of the recesses in the array 50 have the same configuration. However, it is contemplated that some of the recesses in the array 50 may have configurations which are different than the configuration of other recesses in the array 50.

Each of the recesses 56 has a rim portion 70 (FIG. 3) formed by a polygonal array of interconnected rim sections 72, 74, 76 and 78. The linear rim sections 72-78 are interconnected to form a polygonal array of rim sections (FIG. 3). In the illustrated embodiment of the recesses 56, the rim sections 72-78 are interconnected to form a rectangular array. In the embodiment of FIG. 3, each of the rim sections 72-78 has the same length. Therefore, the rectangular array of rim sections has a square configuration. However, it is contemplated that the rim sections may be interconnected to form a rim portion 70 having a different configuration, for example, a triangular or hexagonal configuration. Rather than having linear rim sections 72-78, the recesses 56 may be provided with arcuate rim sections.

Each of the rim sections 72-78 has a continuous arcuate outer side surface, as viewed in a plane extending perpendicular to a central axis of the rim section. Thus, the opposite rim sections 74 and 78 (FIGS. 3 and 4) have continuous arcuate outer side surfaces 84 and 86. Similarly, the rim sections 72 and 76 (FIGS. 3 and 5) have continuous arcuate outer side surfaces 88 and 90. The configuration of the outer side surfaces 84 and 86 of the rim sections 74 and 78 is the same as the configuration of the outer side surfaces 88 and 90 of the rim sections 72 and 76. However, it is contemplated that the rim sections 74 and/or 78 may have outer side surfaces 84 and/or 86 with a configuration which is different than the configuration of the outer side surfaces 88 and/or 90 of the rim sections 72 and/or 76.

Figure 4:
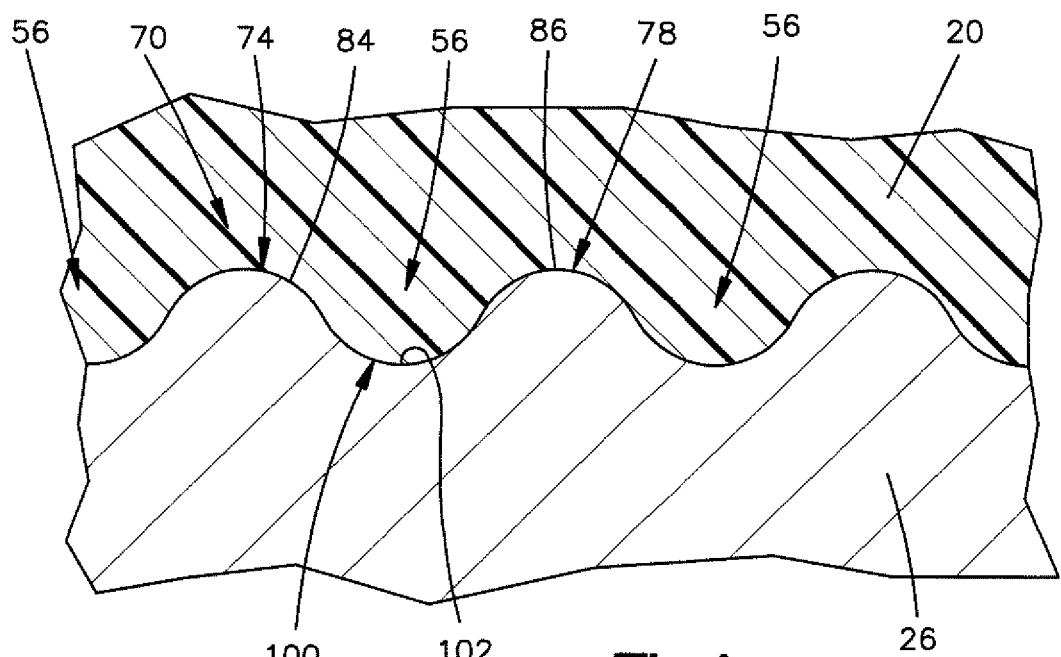
FIG. 4 is an enlarged schematic fragmentary sectional view, taken generally along the line 4-4 of FIG. 3, further illustrating the construction of recesses which form part of the array of recesses formed in the lower plate of the artificial disc of FIG. 1.
Figure 5:
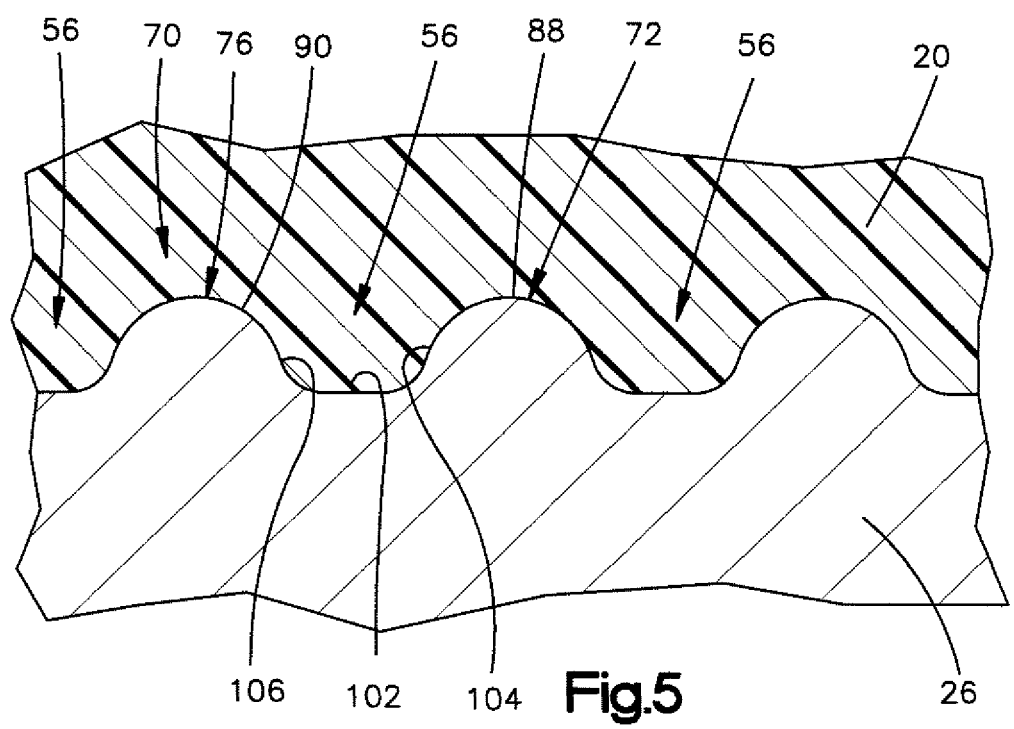
FIG. 5 is an enlarged schematic fragmentary sectional view, taken generally along the line 5-5 of FIG. 3, further illustrating the construction of recesses which form part of the array of recesses formed in the lower plate of the artificial disc of FIG. 1.

The outer side surfaces 84-90 of the rim sections 72-78 have continuously curving cross-sectional configurations as viewed in planes extending perpendicular to longitudinal central axes of the rim sections, that is, as viewed in FIGS. 4 and 5. The outer side surfaces 84-90 of the rim sections 72-78 are free of discontinuities. Therefore, there are no stress inducing corners in the surfaces of 84-90 of the rim sections 72-78. However, as was previously mentioned, the outer side surfaces 84-90 of the rim sections 72-78 may be etched to promote a secure connection between the resilient core 20 and the lower plate 26.

The outer side surfaces 84-90 of the rim sections 72-78 of one of the recesses 56 form continuations of outer side surfaces of rim sections of adjacent recesses. Thus, the outer side surface 84 of the rim section 74 forms a continuation of the outer side surfaces on the rim section of the recess 56 disposed to the left (as viewed in FIG. 4) of the rim section 74. Similarly, the outer side surface 86 of the rim section 78 forms a continuation of the outer side surface on the rim section of the recess 56 disposed to the right (as viewed in FIG. 4) of the rim section 78.

The outer side surface 88 of the rim section 72 (FIG. 5) forms a continuation of the outer side surface of the rim section of the recess 56 disposed to the right (as viewed in FIG. 5) of the rim section 72. Finally, the outer side surface 90 of the rim section 76 forms a continuation of the outer side surface of the rim section of the recess 56 disposed to the left (as viewed in FIG. 5) of the rim section 76. By having the continuously curving outer side surfaces of the rim sections of one recess 56 form continuations of outer side surfaces of rim sections of adjacent recesses, the formation of stress inducing discontinuities between rim sections of adjacent recesses is avoided.

However, it should be understood that the recesses 56 may be formed in such a manner as to have surfaces, which are not continuously curving, between rim portions 70 of adjacent recesses 56. For example, a flat surface area may be provided between rim portions of adjacent recesses. Alternatively, curving surface areas with arcs of curvature which are different than the arcs of curvature of the outer side surfaces 84-90 of the rim sections 72-78 of one recess may be provided between the rim portion of one recess and the rim portion of adjacent recesses. As another alternative, peaks may be provided between the rim portions of adjacent recesses 56. As another alternative, sections having a polygonal cross sectional configuration (as viewed in FIGS. 4 and 5) may be provided between the rim portions of adjacent recesses 56.

Each of the recesses 56 (FIG. 3) includes a bottom portion 100 having a generally polygonal configuration, as viewed in FIG. 3. The rim portion 70 extends around the bottom portion 100. The rim portion 70 has the same polygonal configuration as the bottom portion 100. Thus, in the specific embodiment of the invention illustrated in FIG. 3, both the rim portion 70 and bottom portion 100 have rectangular configurations. However, it should be understood that the bottom portion 100 may have a configuration which is different than the configuration of the rim portion 70. For example, the bottom portion 100 may have a circular configuration while the rim portion 70 has a polygonal configuration. Alternatively, the rim portion 70 may have a circular configuration while the bottom portion 100 has a rectangular configuration.

In the embodiment of the recesses 56 illustrated in FIG. 3, the bottom portion 100 includes a continuously curving major side surface 102 and first and second minor side surfaces 104 and 106. If desired, a greater number of minor side surfaces may be provided in the bottom portion 100 of each of the recesses 56. Alternatively, the minor side surfaces may be eliminated and a single major side surface utilized to form the entire bottom portion 100 of a recess 56. If desired, the bottom portion 100 of a recess 56 may be formed with a generally hemispherical configuration. Alternatively, the bottom portion 100 of a recess 56 may be formed with an oval and continuously curving configuration.

The major side surface 102 (FIGS. 3-5) of the bottom portion 100 of a recess 56 is formed as a continuation of the outer side surfaces 84 and 86 of the rim sections 74 and 78 (FIG. 4). The outer side surfaces 84 and 86 of the rim sections 74 and 78 form continuations of the outer side surfaces of adjacent recesses 56 (FIG. 4). Therefore, the major side surface 102 of the bottom portion of one recess is formed as a continuation of the major side surfaces of the bottom portions of adjacent recesses (FIG. 4). This results in the rim sections 76 and 78 cooperating with the bottom portion 100 to form a uniformly undulating and generally sinusoidal wave configuration as viewed in a plane extending perpendicular to the central axes of the rim sections 74 and 78.

The sinusoidal wave (as viewed in FIG. 4) formed by the adjacent recesses 56 is free of stress inducing discontinuities. However, it should be understood that the outer side surfaces 84 and 86 of the rim sections 74 and 78 may cooperate with the major side surface 102 of the bottom portion 100 having a shape which is different than the illustrated shape. For example, the waves viewed in the plane of FIG. 4 may have the same configuration as the waves of FIG. 5. As another example, the surfaces may cooperate to form nonuniform or irregular waves.

In the illustrated embodiment of the invention, the rim portions 70 and bottom portions 100 of the recesses 56 cooperate to form a series of identical waves having the same wavelength or frequency. However, it should be understood that the rim portions 70 and bottom portions 100 of the recesses 56 may cooperate to form waves which are not identical. For example, the waves may have different frequencies or wavelengths. Alternatively, the wave may have an irregular wave form. As another example, the waves may have different amplitudes.

The recesses 56 form the waves of FIGS. 4 and 5 with equal wavelengths and amplitudes. These specific waves have a two millimeter (2 mm) wavelength and a 0.5 millimeter amplitude. The thickness of the lower plate 26, as measured from a tangent to the crest of a wave formed in FIG. 4 or 5 to the bottom side of the lower plate is 1.0 millimeter. However, it should be understood that the waves of FIGS. 4 and 5 may have dimensions other than these specific dimensions and that the lower plate 26 may have a thickness other than this specific thickness. For example, the wavelength and/or amplitude of the wave of FIG. 4 may be larger or smaller than the wavelength and/or amplitude of the wave of FIG. 5. The lower plate 26 may be formed with any one of many different permutations and combinations of plate thickness, wavelengths and wave amplitudes.

Although only the lower plate 26 has been illustrated in FIGS. 2 through 5, it should be understood that the upper plate 24 has the same construction as the lower plate 26. Thus, the upper plate 24 has an upwardly domed or curving configuration, that is, a curved configuration in a direction toward the upper vertebra 12. The inner side, the lower side as viewed in FIG. 1, of the upper plate 24 is provided with an array of recesses, corresponding to the array 50 of recesses in the lower plate 26. The array of recesses in the lower (as viewed in FIG. 1) side of the upper plate 24 includes a plurality of recesses, corresponding to the plurality 54 of recesses. The plurality of recesses in the lower side of the upper plate 24 have configurations corresponding to the configuration of the recesses 56 of FIGS. 3-5.

It should be understood that one of the upper and lower plates 24 and 26 may have an inner side with a configuration which is different than the illustrated configuration of the inner side 38 of the lower plate 26. It should also be understood that one or both of the upper and lower plates 24 and 26 may have recesses with configurations which are different than the configuration of the recesses 56 of FIGS. 3-5. If desired, the construction of the upper plate 24 may be different than the construction of the lower plate 26.

Alternative Arrays of Recesses

Figure 6:
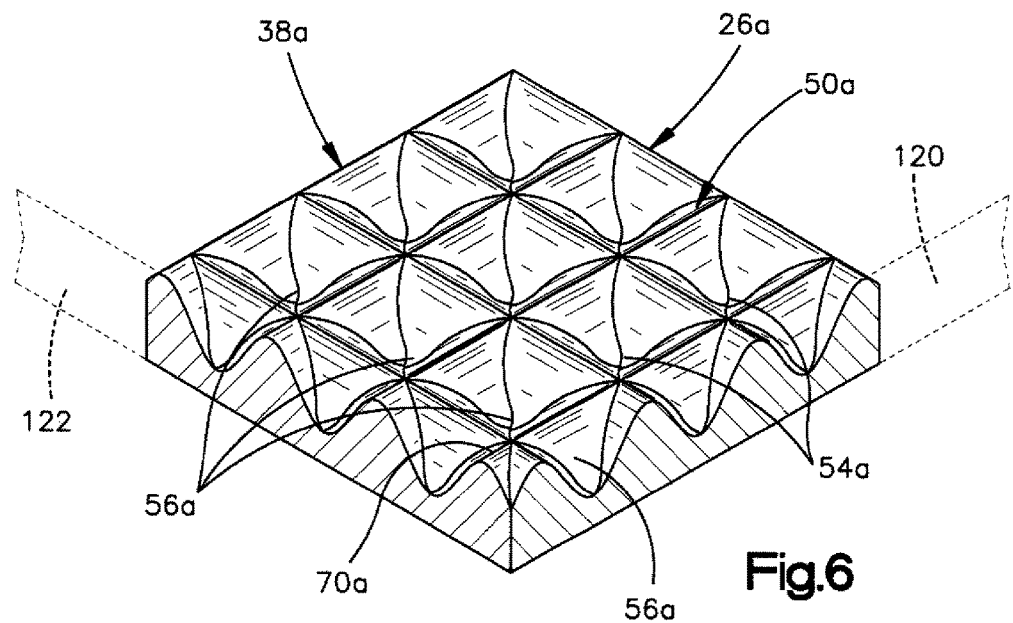
FIG. 6 is a schematic fragmentary plan view of another embodiment of recesses which may be formed in the lower plate of the artificial disc of FIG. 1.

In the embodiment of the invention illustrated in FIGS. 1-5, the plurality 54 of recesses 56 have different cross sectional configurations as viewed in perpendicular cross sectional planes. Thus, in the plane taken along the line 4-4 of FIG. 3, the recesses 56 have a uniformly undulating configuration which may be referred to as being sinusoidal. In the plane taken generally along the line 5-5 of FIG. 3, the recesses 56 have arcuately curving crests or rim portions and troughs which are, as viewed in FIG. 5, linear. Since the embodiment of the invention illustrated in FIG. 6 is generally similar to the embodiment of the invention illustrated in FIGS. 1-5, similar numerals will be utilized to designate similar components. The suffix letter "a" being associated with the numerals of FIG. 6 to avoid confusion.

A lower plate 26a (FIG. 6) having the same general construction as the lower plate 26 of FIG. 2, is used in an artificial disc having the same general construction as the artificial disc 10 of FIG. 1. The lower plate 26a (FIG. 6) includes an inner side 38a. The inner side 38a of the lower plate 26a includes an array 50a of recesses. The array 50a of recesses includes a plurality 54a of recesses 56a.

The recesses 56a have the same cross-sectional configuration when viewed in planes extending perpendicular to each other. The recesses 56 of FIGS. 3-5 have the configuration illustrated in FIG. 4 when viewed along the cross sectional plane designated 4-4 in FIG. 3. The recesses 56 have a different configuration when viewed along the cross sectional plane designated 5-5 in FIG. 3. However, the recesses 56a of FIG. 6 have the same configuration when viewed in the cross sectional plane corresponding to the plane 4-4 of FIG. 3 and when viewed in the cross sectional plane corresponding to the plane 5-5 of FIG. 3. Thus, in FIG. 6, the configuration of the recesses as viewed in a cross sectional plane 120 has the same configuration as when viewed in a cross sectional plane 122. The two cross sectional planes 120 and 122 extend perpendicular to each other.

The surfaces of the recesses 56a form a uniformly undulating and generally sinusoidal wave as viewed in the plane 120 of FIG. 6. Similarly, the recesses 56a form a uniformly undulating and generally sinusoidal wave, as viewed in the cross sectional plane 122 of FIG. 6. The recesses 56a are formed by uniformly curving surfaces which are free of discontinuities. Although the recesses 56a have a uniform polygonal configuration, specifically, a square configuration, it is contemplated that the recesses 56a may have a different configuration if desired. For example, the recesses 56a may have a circular or oval configuration, when viewed from above, (as viewed in FIG. 6).

Figure 7:
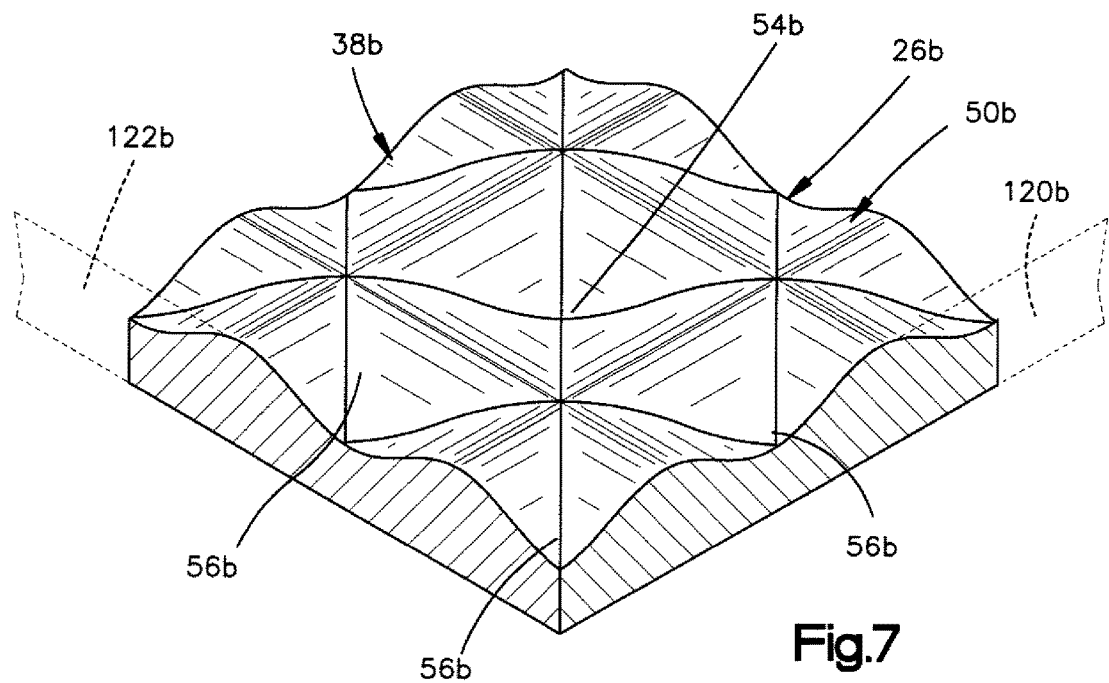
FIG. 7 is a schematic fragmentary plan view, generally similar to FIG. 6, of another embodiment of recesses which may be formed in the lower plate of the artificial disc of FIG. 1.

The embodiment of the invention illustrated in FIG. 7 is generally similar to the embodiments of the invention illustrated in FIGS. 1-6. Therefore, similar components of the invention will be designated by similar numerals, the suffix letter "b" being added to the numerals of FIG. 7 to avoid confusion.

A lower plate 26b of an artificial disc having a construction corresponding to the construction of the artificial disc 10 of FIG. 1 is illustrated schematically in FIG. 7. The lower plate 26b includes an upper side 38b which may be curved or domed in the manner previously explained in conjunction with the embodiment of the invention illustrated in FIGS. 1-5. An array 50b of recesses is formed in the inner side 38b of the lower plate 26b. The array 50b of recesses includes a plurality of recesses 54b.

The plurality of recesses 54b includes recesses 56b which have the same configuration. The recesses 56b have a configuration which is similar to the configurations of the recesses 56a of FIG. 6. The recesses 56b (FIG. 7) have the same cross sectional configuration when viewed in a plane 120b as when viewed in a cross sectional plane 122b. It should be understood that the planes 120b and 122b correspond, generally speaking, to the cross sectional planes designated by the numerals 4 and 5 in FIG. 3. The recesses 56b (FIG. 7) have a uniform undulating configuration as viewed in perpendicular planes designated 120b and 122b. These waves may be referred to as being sinusoidal.

The waves formed by the surfaces of the recesses 56b (FIG. 7) in the plane 120b have the same amplitude (height) as the wave formed by the surfaces of the recesses 56a in the plane 120 of FIG. 6. However, the wave formed by the surfaces of the recesses 56b (FIG. 7) have a wavelength which is twice as great as the wavelength of the wave formed by the surfaces of the recesses 56a (FIG. 6) in the plane 120.

Figure 8:
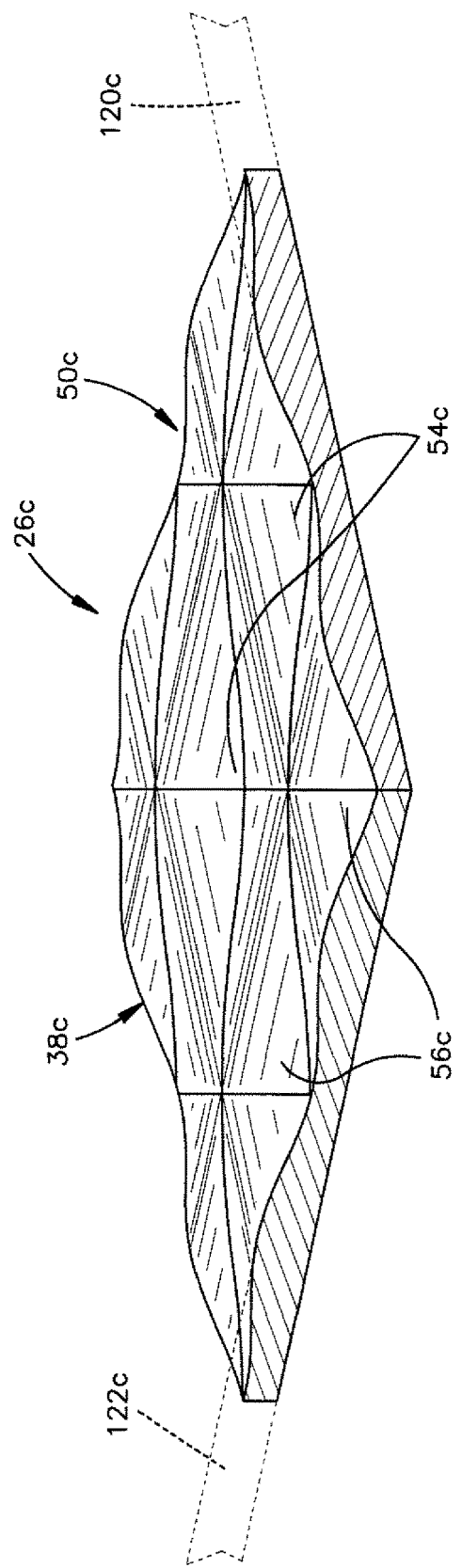
FIG. 8 is a schematic fragmentary plan view, generally similar to FIGS. 6 and 7, of still another embodiment of recesses which may be formed in the lower plate of the artificial disc of FIG. 1.

The embodiment of the invention illustrated in FIG. 8 is generally similar to the embodiments of the invention illustrated in FIGS. 1-7. Therefore, similar numerals will be utilized to designate similar components, the suffix letter "c" being added to the numerals of FIG. 8 to avoid confusion.

A lower plate 26c (FIG. 8) is used in an artificial disc similar to the artificial disc 10 of FIG. 1. The lower plate 26c has an inner side 38c which faces away from a lower vertebra, corresponding to the vertebra 14 of FIG. 1, and is fixedly connected to a resilient core, corresponding to the resilient core 20 of FIG. 1. An array 50c of recesses is formed in the inner side 38c of the lower plate 26c.

The array 50c of recesses includes a plurality 54c of recesses 56c having the same configuration. Surfaces of the recesses 56c form a uniformly undulating wave, which may be referred to as a sine wave, when the recesses are viewed in a cross sectional plane 120c corresponding to the cross sectional plane designated by the numerals 4-4 in FIG. 3. Similarly, the recesses 56c form a uniformly undulating wave when the recesses are viewed in a cross sectional plane 122c corresponding to the cross sectional plane 5-5 of FIG. 3. The recesses 56c have a wavelength which is three times as great as the wavelength of the recesses 56a of FIG. 6. However, the recesses 56c have the same amplitude or height as the recesses 56a of FIG. 6.

Figure 9:
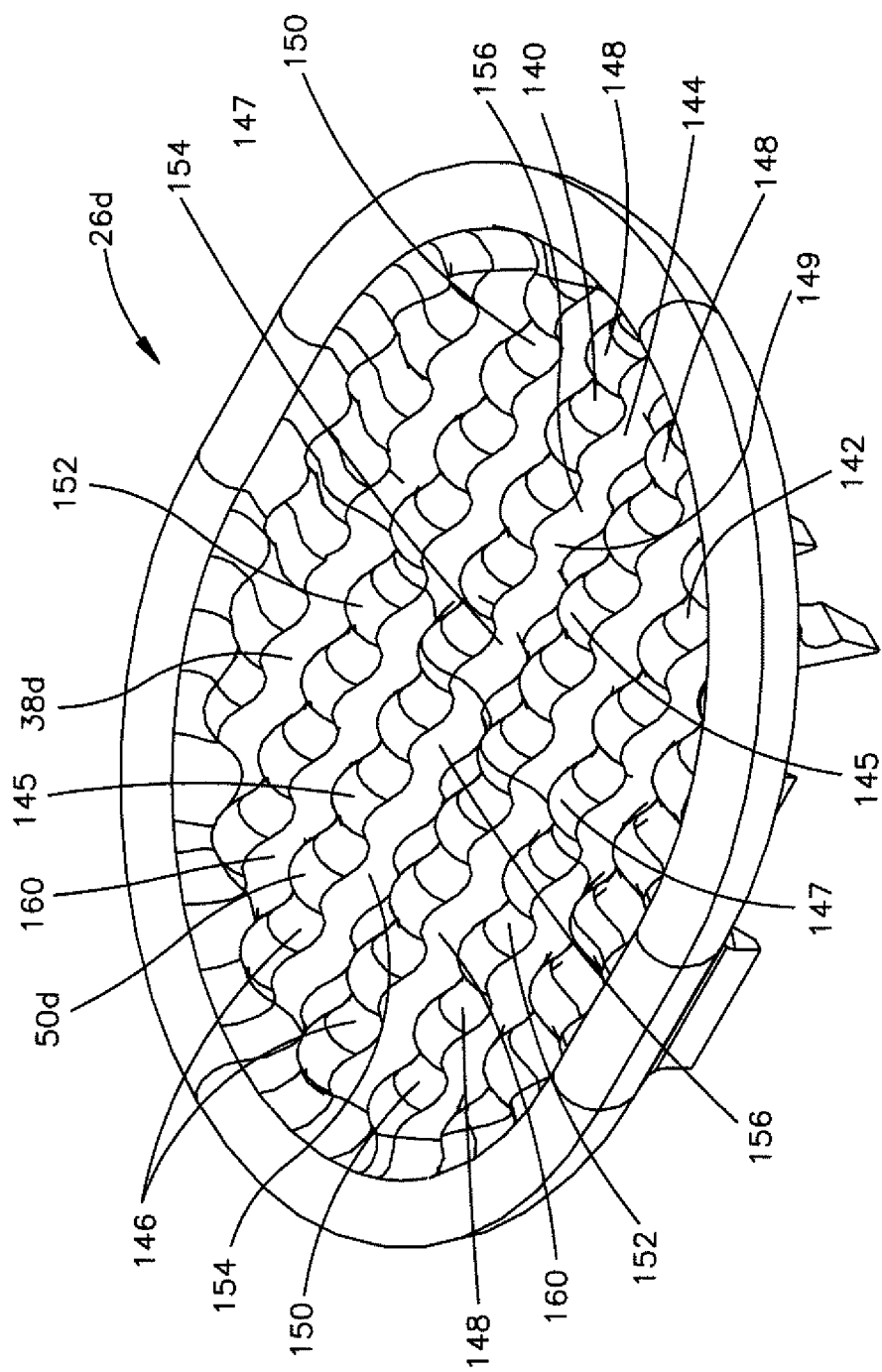
FIGS. 9-11 are schematic views of another embodiment of a plate for use in the artificial disc of FIG. 1.
Figure 10:
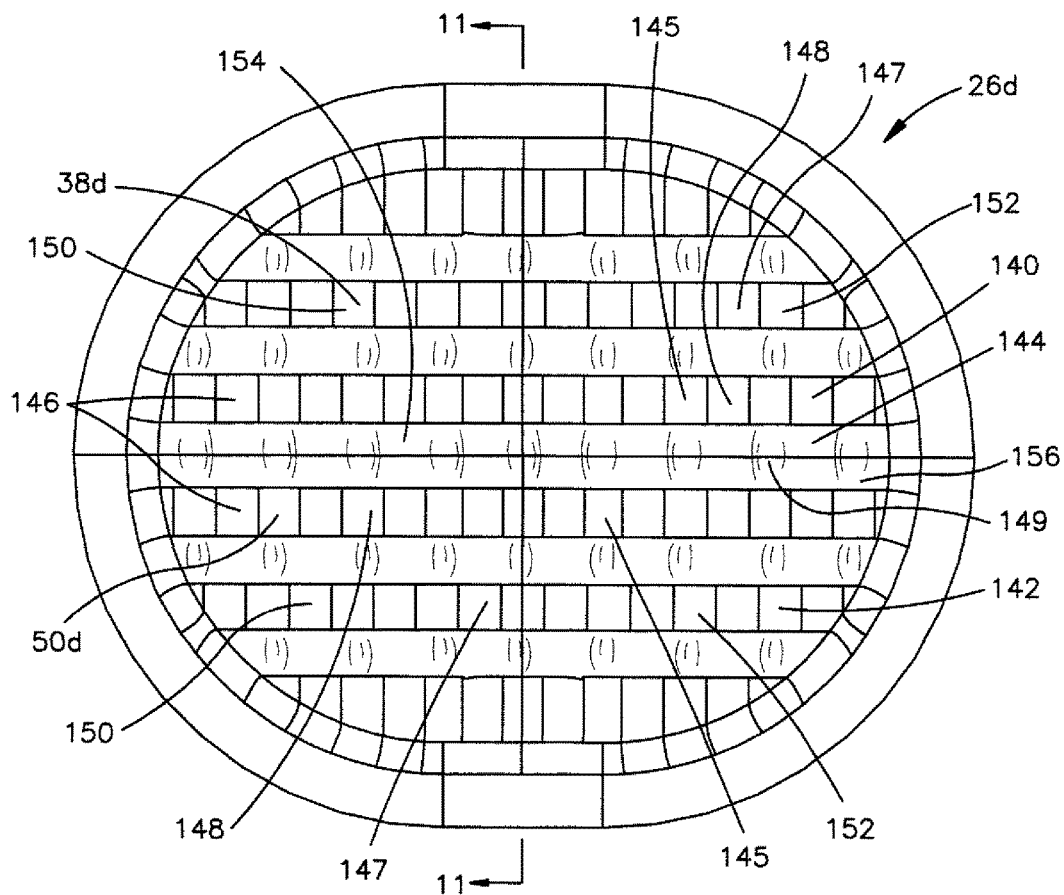
Figure 11:
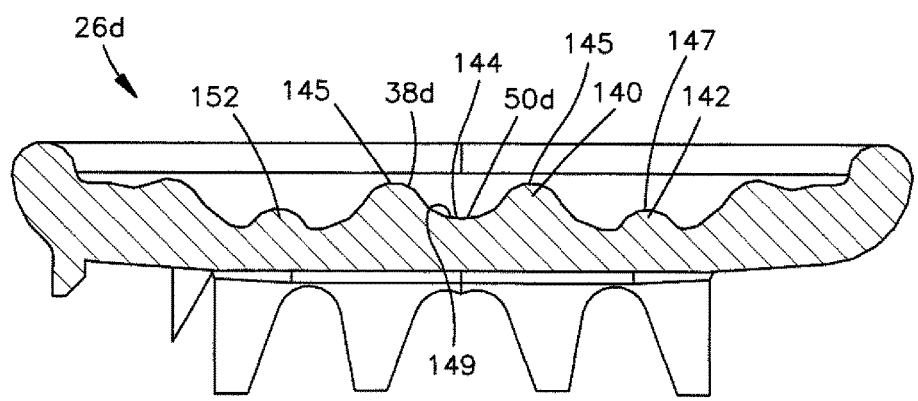

The embodiment of the invention illustrated in FIGS. 9-11 is generally similar to the embodiments of the invention illustrated in FIGS. 1-8. Therefore, similar components of the invention will be designated by similar numerals, the suffix letter "d" being added to the numerals of FIGS. 9-11 to avoid confusion.

A lower plate 26d (FIGS. 9-12) is used in an artificial disc similar to the artificial disc 10 of FIG. 1. The lower plate 26d has an inner side 38d which faces away from a lower vertebra, corresponding to the vertebra 14 of FIG. 1, and is fixedly connected to a resilient core, corresponding to the resilient core 20 of FIG. 1. An array 50d of recesses is formed in the inner side 38d of the lower plate 26d. The array 50d of recesses includes a first set of recesses 140, a second set of recesses 142 and a third set of recesses 144. Although the plate 26d is described as having three sets of recesses, it is contemplated that the plate may include any desired numbers of sets of recesses.

The first set of recesses 140 are at least partially defined by arcuate surfaces 145. The arcuate surfaces 145 and the first set of recesses 140 form a uniformly undulating wave, which may be a sine wave, when the recesses are viewed in a cross sectional plane. The second set of recesses 142 are at least partially defined by arcuate surfaces 147. The arcuate surfaces 147 and the second set of recesses 142 form a uniformly undulating wave, which may be a sine wave, when the recesses are viewed in a cross sectional plane. The third set of recesses 144 are at least partially defined by arcuate surfaces 149. The arcuate surfaces 149 and the third set of recesses 144 form a uniformly undulating wave, which may be a sine wave, when the recesses are viewed in a cross sectional plane.

The arcuate surfaces 145 and the first set of recesses 140 form an undulating wave having an amplitude greater than the amplitudes of the undulating waves formed by the arcuate surfaces 147, 149 and the second and third set of recesses 142, 144. The amplitude of the undulating waves formed by the arcuate surfaces 147 and the second set of recesses 142 may be approximately the same as the amplitude of the undulating waves formed by arcuate surfaces 149 and the third set of recesses 144. It is contemplated that the amplitudes of the undulating waves formed by the first, second and third sets of recesses may have any desired amplitude and may have the same amplitudes.

The first set of recesses 140 includes a plurality of recesses 146 in rows 148. The rows 148 of recesses 146 extend generally parallel to each other. The second set of recesses 142 includes a plurality of recesses 150 in rows 152. The rows 152 of recesses 150 extend generally parallel to each other and generally parallel to the rows 148 of the first set of recesses 140. The third set of recesses 144 includes a plurality of recesses 154 in a row 156. The row 156 of recesses 154 extends generally parallel to rows 148 and 152.

The first set of recesses 140 includes two rows 148 of recesses 146. The second set of recesses 142 includes two rows 152 of recesses 150. Although each of the first and second sets 140, 142 are shown as including two rows 148, 152 of recesses 146, 150, and the third set of recesses 144 is shown as including only one row 156 of recesses 154, it is contemplated that each of the first, second and third sets of recesses may include any desired number of rows of recesses. It is also contemplated that each of the rows 148, 152, 156 may include any number of recesses 146, 150, 154.

The rows 148 of the first set of recesses 140 are located between the rows 152 of the second set of recesses 142. The row 156 of the third set of recesses 144 is located between the rows 148 of the first set of recesses 140. A plurality of channels 160 extend parallel to the rows 148, 152, 156. At least one channel 160 is located between adjacent rows 148 and 152. The channels 160 have surfaces that transition between the rows 148, 152 of the first and second sets of recesses 140, 142.

The crests and troughs of the undulating waves formed by arcuate surfaces 145 and the first set of recesses 140 are aligned with the crests and troughs of the undulating wave formed by the arcuate surfaces 149 and the third set of recesses 144. The crests of the undulating waves formed by the arcuate surfaces 147 and the second set of recesses 142 are aligned with the crests of the undulating waves formed by the arcuate surfaces 145, 149 and the first and third set of recesses 140, 144. The troughs of the undulating waves formed the arcuate surfaces 147 and the second set of recesses 142 are aligned with crests of the undulating waves formed by the first and third set of recesses 140, 144. Therefore, the wavelengths of the undulating waves formed by the first, second and third sets of recesses 140, 142, 144 are the same. It is contemplated that the undulating waves formed by the first, second and third sets of the recesses 140, 142, 144 may have any desired wavelengths and may differ from each other.

The arcuate surfaces 145, 147, 149 and the recesses 146, 150, 154 have continuously curving cross-sectional configurations. The arcuate surfaces 145, 147, 149 and the recesses 146, 150, 154 are free of discontinuities. Therefore, there are no stress inducing corners in the arcuate surfaces of 145, 147, 149 and the recesses 146, 150, 154.

Figure 12:
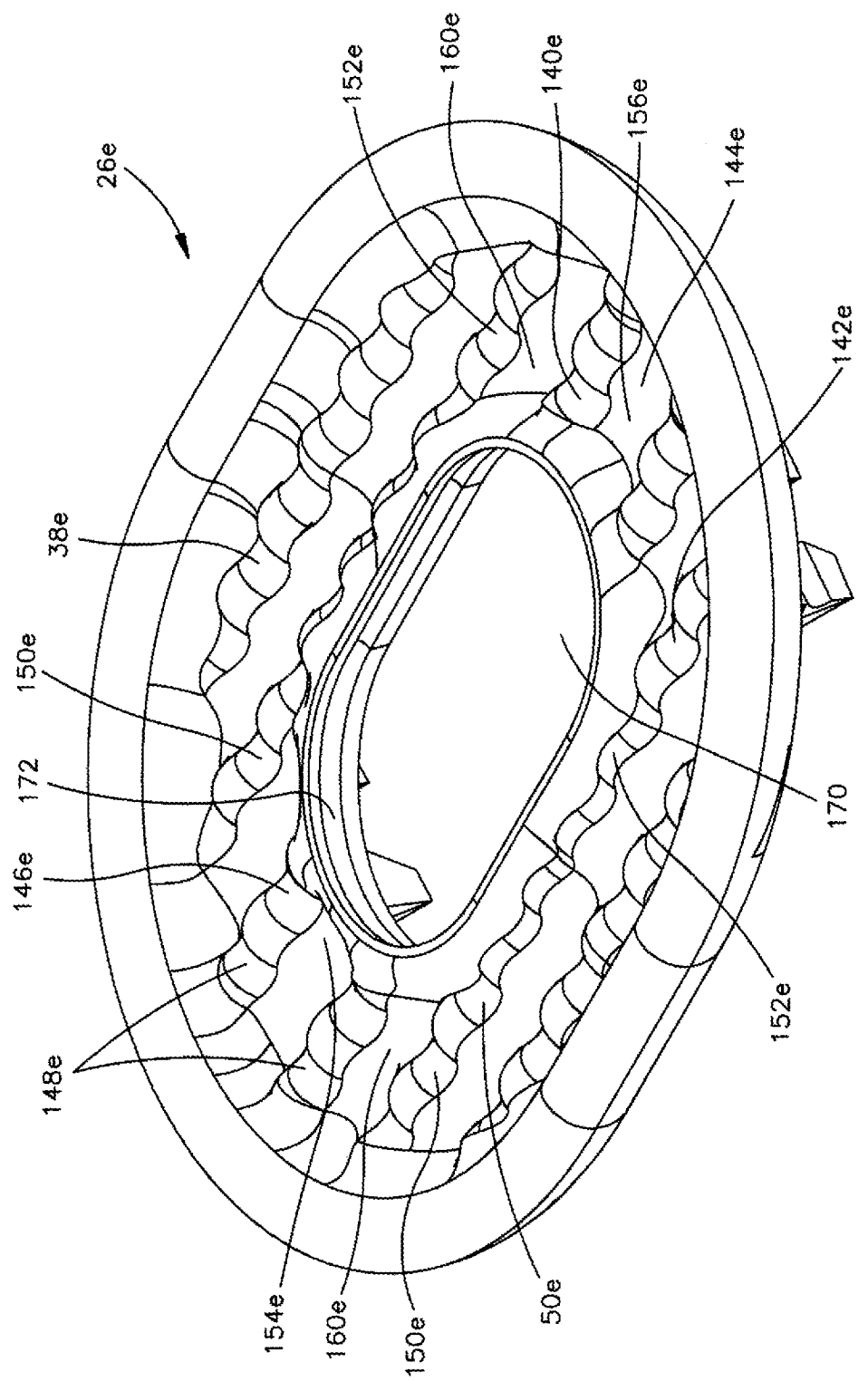
FIG. 12 is a schematic view of another embodiment of a plate for use in the artificial disc of FIG. 1.

The embodiment of the invention illustrated in FIG. 12 is generally similar to the embodiment of the invention illustrated in FIGS. 9-11. Therefore, similar components of the invention will be designated by similar numerals, the suffix letter "e" being added to the numerals of FIG. 12 to avoid confusion. The embodiment illustrated in FIG. 12 differs from the embodiment illustrated in FIGS. 9-11 in that an opening extends through the plate.

A lower plate 26e (FIG. 12) is used in an artificial disc similar to the artificial disc 10 of FIG. 1. The lower plate 26e has an inner side 38e which faces away from a lower vertebra, corresponding to the vertebra 14 of FIG. 1, and is fixedly connected to a resilient core, corresponding to the resilient core 20 of FIG. 1. An array 50e of recesses is formed in the inner side 38e of the lower plate 26e. The array 50e of recesses includes a first set of recesses 140e, a second set of recesses 142e and a third set of recesses 144e. Although the plate 26e is described as having three sets of recesses, it is contemplated that the plate may include any desired number of sets of recesses.

The first set of recesses 140e includes a plurality of recesses 146e in rows 148e. The rows 148e of recesses 146e extend generally parallel to each other. The second set of recesses 142e includes a plurality of recesses 150e in rows 152e. The rows 152e of recesses 150e extend generally parallel to each other and generally parallel to the rows 148e of the first set of recesses 140e. The third set of recesses 144e includes a plurality of recesses 154e in a row 156e. The row 156e of recesses 154e extends generally parallel to rows 148e and 152e. A plurality of channels 160e extend parallel to the rows 148e, 152e, 156e. At least one channel 160e is located between adjacent rows 148e and 152e.

The plate 26e has a central opening 170 extending through the plate. If desired, the opening 170 may receive a member (not shown) to close the opening. A recess 172 may extend around the opening 170 for connecting the member to the plate 26e. The opening 170 may have a configuration other than the illustrated oval configuration.

Figure 13:
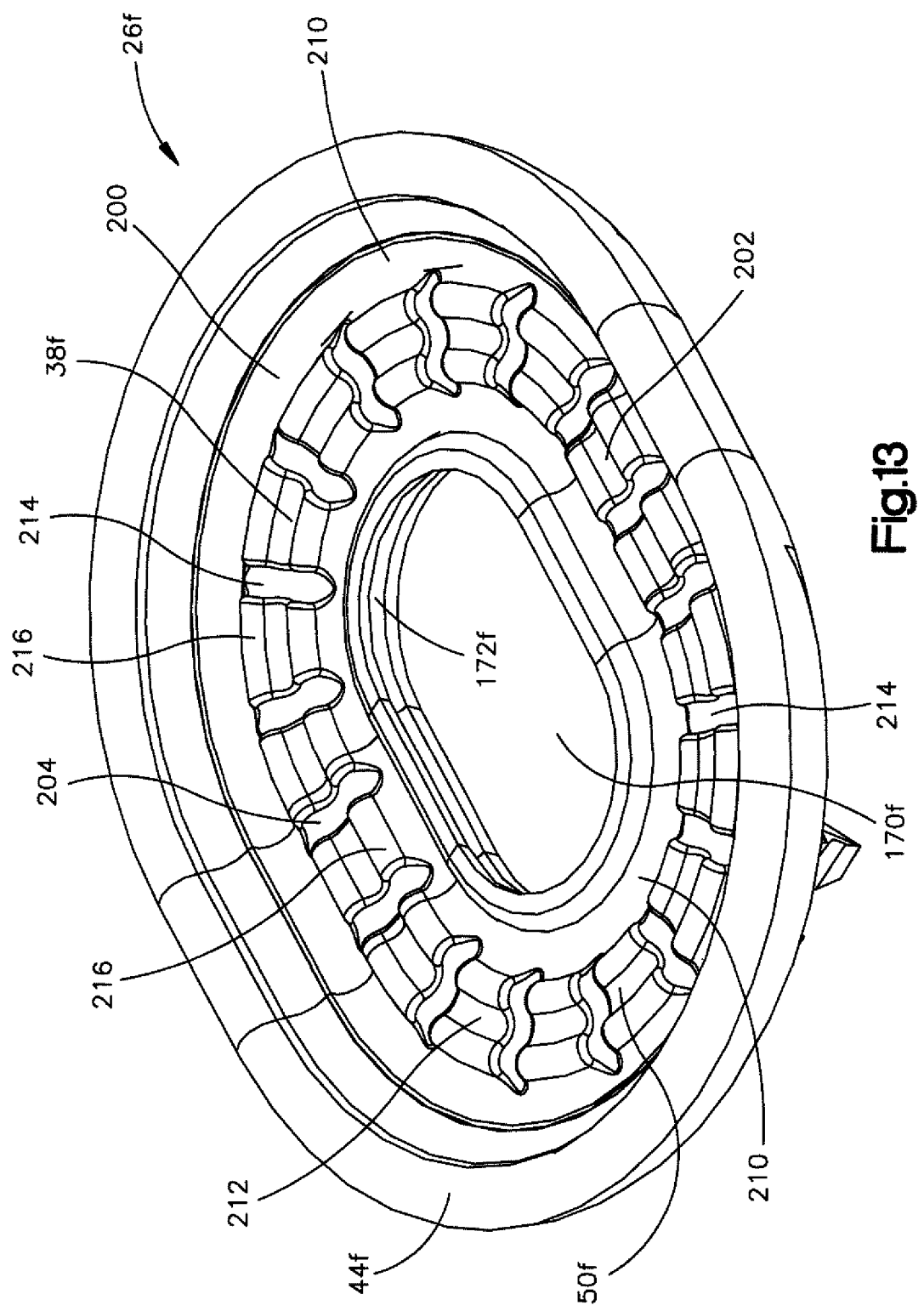
FIGS. 13-15 are schematic views of another embodiment of a plate for use in the artificial disc of FIG. 1.
Figure 14:
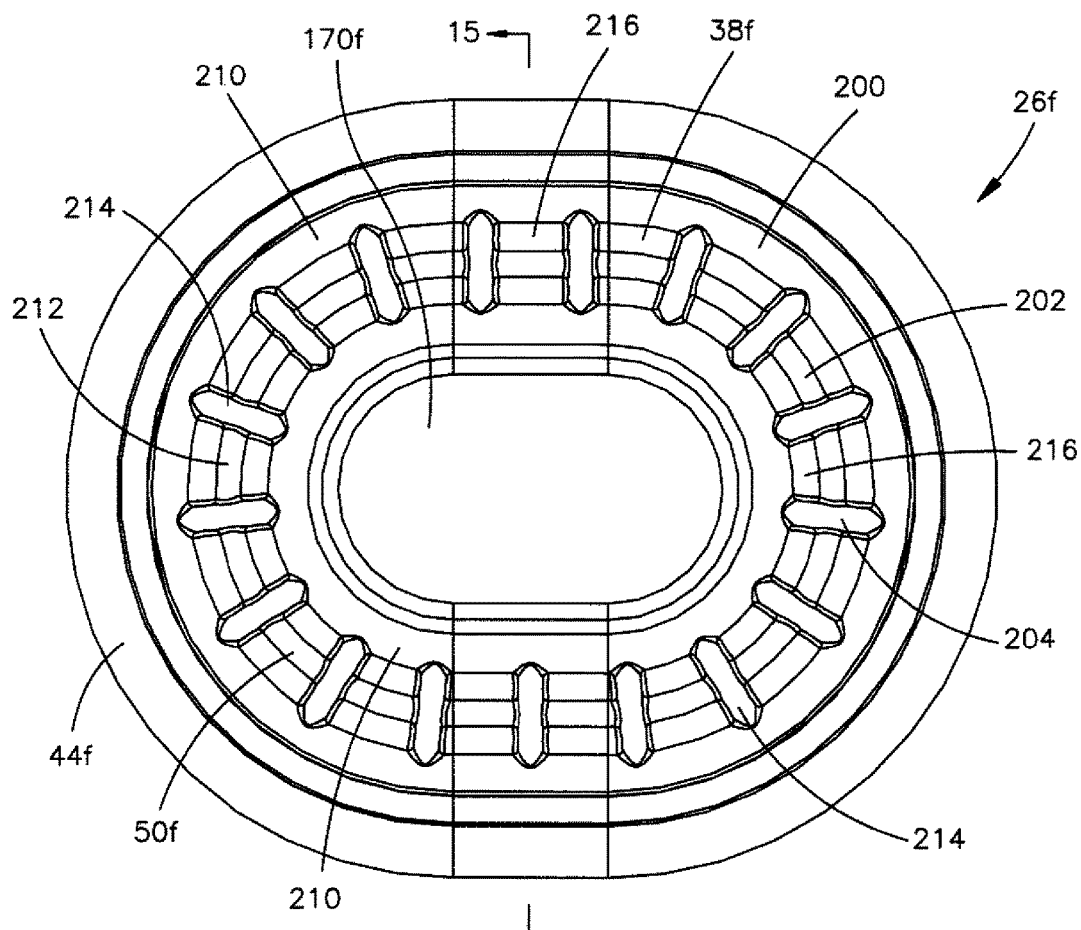
Figure 15:
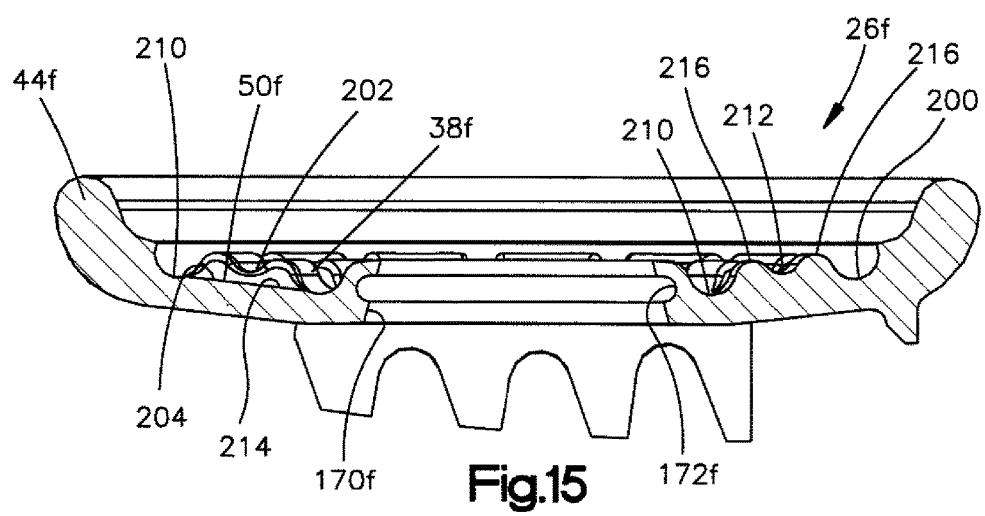

The embodiment of the invention illustrated in FIGS. 13-15 is generally similar to the embodiments of the invention illustrated in FIGS. 1-12. Therefore, similar components of the invention will be designated by similar numerals, the suffix letter "f" being added to the numerals of FIGS. 13-15 to avoid confusion.

A lower plate 26f (FIGS. 13-15) is used in an artificial disc similar to the artificial disc 10 of FIG. 1. The lower plate 26f has an inner side 38f which faces away from a lower vertebra, corresponding to the vertebra 14 of FIG. 1, and is fixedly connected to a resilient core, corresponding to the resilient core 20 of FIG. 1. An array 50f of recesses is formed in the inner side 38f of the lower plate 26f. The array 50f of recesses includes a first set of recesses 200, a second set of recesses 202 and a third set of recesses 204. Although the plate 26f is described as having three sets of recesses, it is contemplated that the plate may include any desired number of sets of recesses.

The first set of recesses 200 includes concentric recesses 210. The recesses 210 are concentric with the peripheral rim 44f of the lower plate 26f. The second set of recesses 202 includes a recess 212 concentric with the recesses 210 and the peripheral rim 44f. Although the concentric recesses 210, 212 and the peripheral rim 44f are shown as having a generally oval shape, it is contemplated that the recesses and the peripheral rim may have any desired shape. Furthermore, the plate 26f may have any desired number of concentric recesses 210, 212 even though the plate is shown as having two concentric recesses 210 and one recess 212. The concentric recesses 210, 212 are at least partially defined by arcuate surfaces 216 extending between the recesses.

The third set of recesses 204 includes a plurality of recesses 214 extending generally transverse to the concentric recesses 210, 212. The recesses 214 extend generally perpendicular to the concentric recesses 210, 212. However, the recesses 214 may extend in any desired direction that is transverse to the concentric recesses 210, 212. The recesses 214 intersect the concentric recesses 210, 212. Although seventeen equally spaced recesses 214 are shown, it is contemplated that the plate 26f may have any desired number of recesses 214 spaced apart in any desired manner.

The recesses 210 and 214 have the same depth. The recess 212 has a depth that is less than the depth of the recesses 210 and 214. Therefore, the recesses 210 and 212 form a undulating wave as seen in cross-section shown in FIG. 15. It is contemplated that the recesses 210, 212 and 214 may have any desired depth. The recesses 210, 212 and 214 may all have different depths or the same depth if desired.

The arcuate surfaces 216 and the recesses 210, 212, 214 have continuously curving cross-sectional configurations. The arcuate surfaces 216 and the recesses 210, 212, 214 are free of discontinuities. Therefore, there are no stress inducing corners in the arcuate surfaces of 216 and the recesses 210, 212, 214.

The plate 26f may have a central opening 170f extending through the plate. The opening 170f may receive a member (not shown) to close the opening. A recess 172f may extend around the opening 170f for connecting the member to the plate 26f. The opening 170f may have a configuration other than the illustrated oval configuration.

Figure 16:
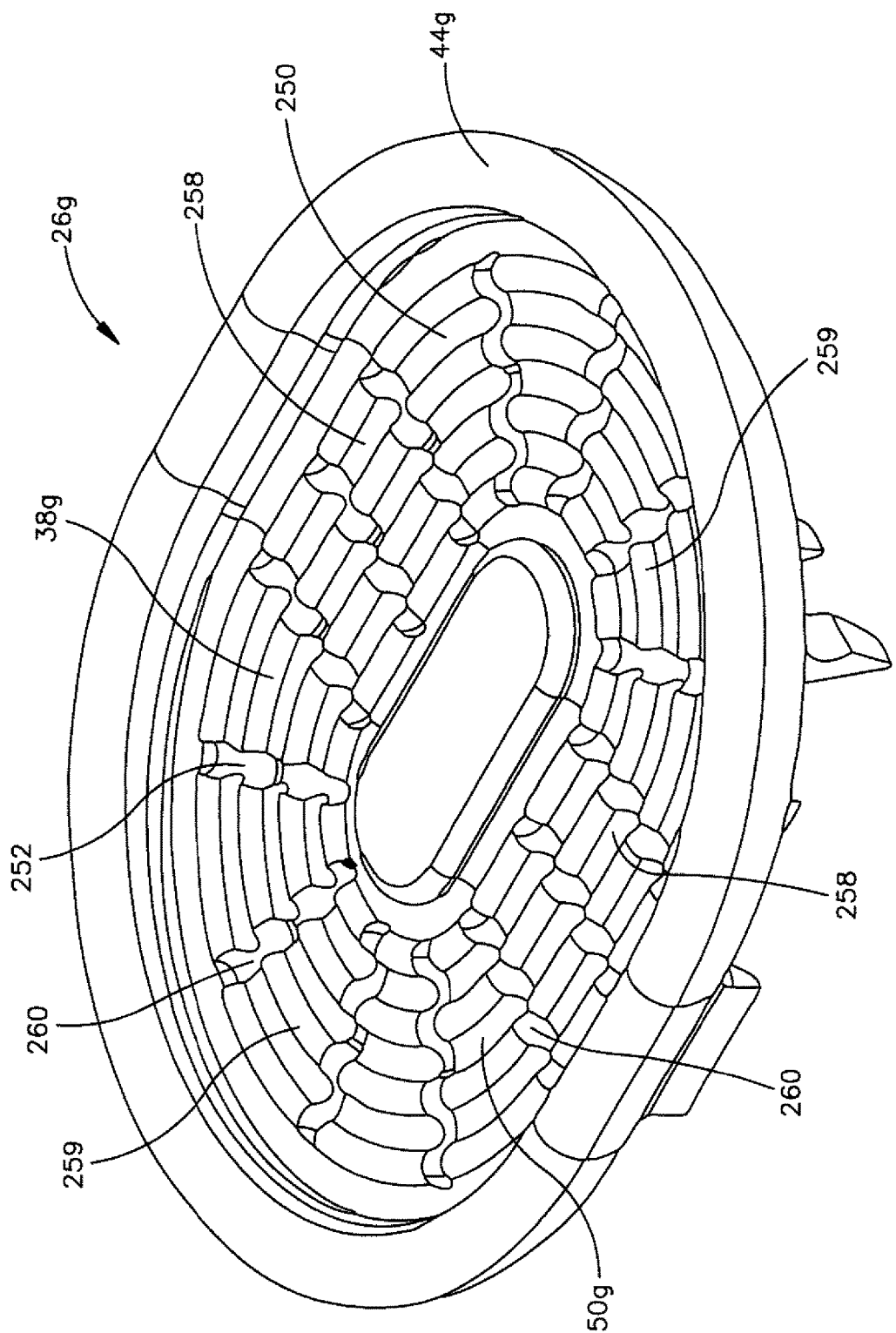
FIGS. 16-18 are schematic views of another embodiment of a plate for use in the artificial disc of FIG. 1.
Figure 17:
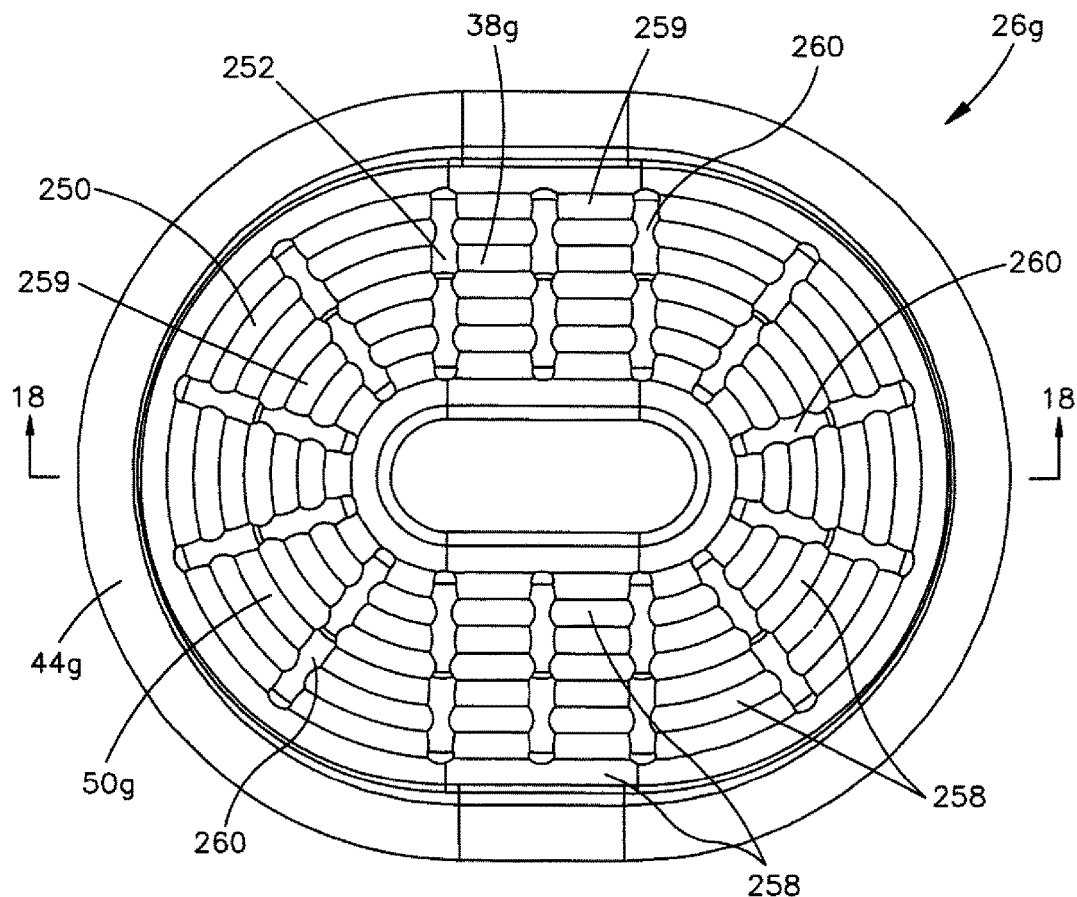
Figure 18:
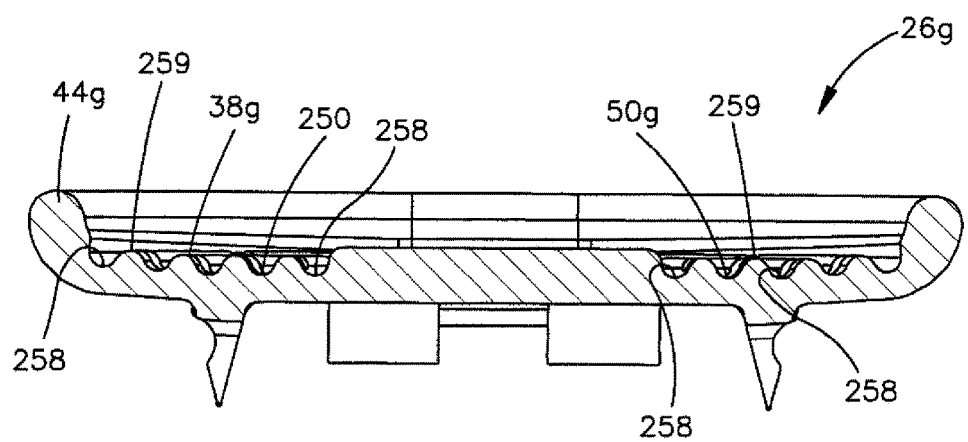

The embodiment of the invention illustrated in FIGS. 16-18 is generally similar to the embodiments of the invention illustrated in FIGS. 1-15. Therefore, similar components of the invention will be designated by similar numerals, the suffix letter "g" being added to the numerals of FIGS. 16-18 to avoid confusion.

A lower plate 26g (FIGS. 16-18) is used in an artificial disc similar to the artificial disc 10 of FIG. 1. The lower plate 26g has an inner side 38g which faces away from a lower vertebra, corresponding to the vertebra 14 of FIG. 1, and is fixedly connected to a resilient core, corresponding to the resilient core 20 of FIG. 1. An array 50g of recesses is formed in the inner side 38g of the lower plate 26g. The array 50g of recesses includes a first set of recesses 250 and a second set of recesses 252. Although the plate 26g is described as having two sets of recesses, it is contemplated that the plate may include any desired number of sets of recesses.

The first set of recesses 250 includes concentric recesses 258. The recesses 258 are concentric with the peripheral rim 44g of the lower plate 26g. Although the concentric recesses 258 and the peripheral rim 44g are shown as having a generally oval shape, it is contemplated that the recesses and the peripheral rim may have any desired shape. Furthermore, the plate 26g may have any desired number of concentric recesses 258 even though the plate is shown as having five concentric recesses. The recesses 258 are at least partially defined by arcuate surfaces 259. The arcuate surfaces 259 and the recesses 258 form an undulating wave as seen in cross-section in FIG. 18.

The second set of recesses 252 includes a plurality of recesses 260 (FIGS. 16-17) extending generally transverse to the concentric recesses 258. The recesses 260 extend generally perpendicular to the concentric recesses 258. However, the recesses 260 may extend in any desired direction that is transverse to the concentric recesses 258. The recesses 260 intersect the concentric recesses 258. The recesses 260 are shown as being equally spaced from each other. However, the recesses 260 may have any desired spacing. Although fourteen recesses 260 are shown in FIG. 17, it is contemplated that the plate 26g may have any desired number of recesses 260.

The recesses 258 and 260 are shown as having the same depth. It is contemplated that the recesses 258, 260 may have any desired depth. The recesses 258, 260 may all have different depths or the same depth if desired.

The arcuate surfaces 259 and the recesses 258, 260 have continuously curving cross-sectional configurations. The arcuate surfaces 259 and the recesses 258, 260 are free of discontinuities. Therefore, there are no stress inducing corners in the arcuate surfaces of 259 and the recesses 258, 260.

Figure 19:
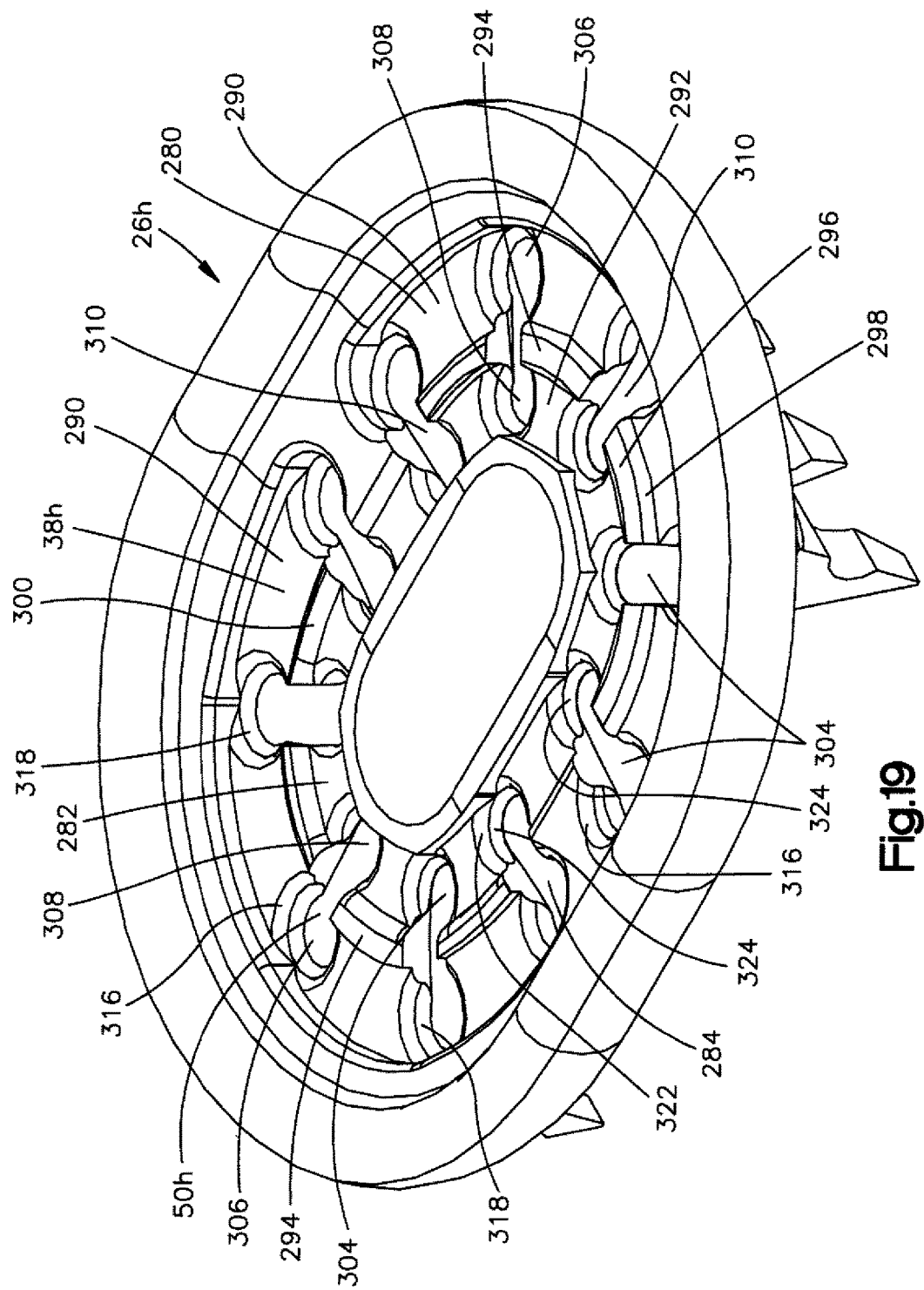
FIGS. 19-21 are schematic views of another embodiment of a plate for use in the artificial disc of FIG. 1.
Figure 20:
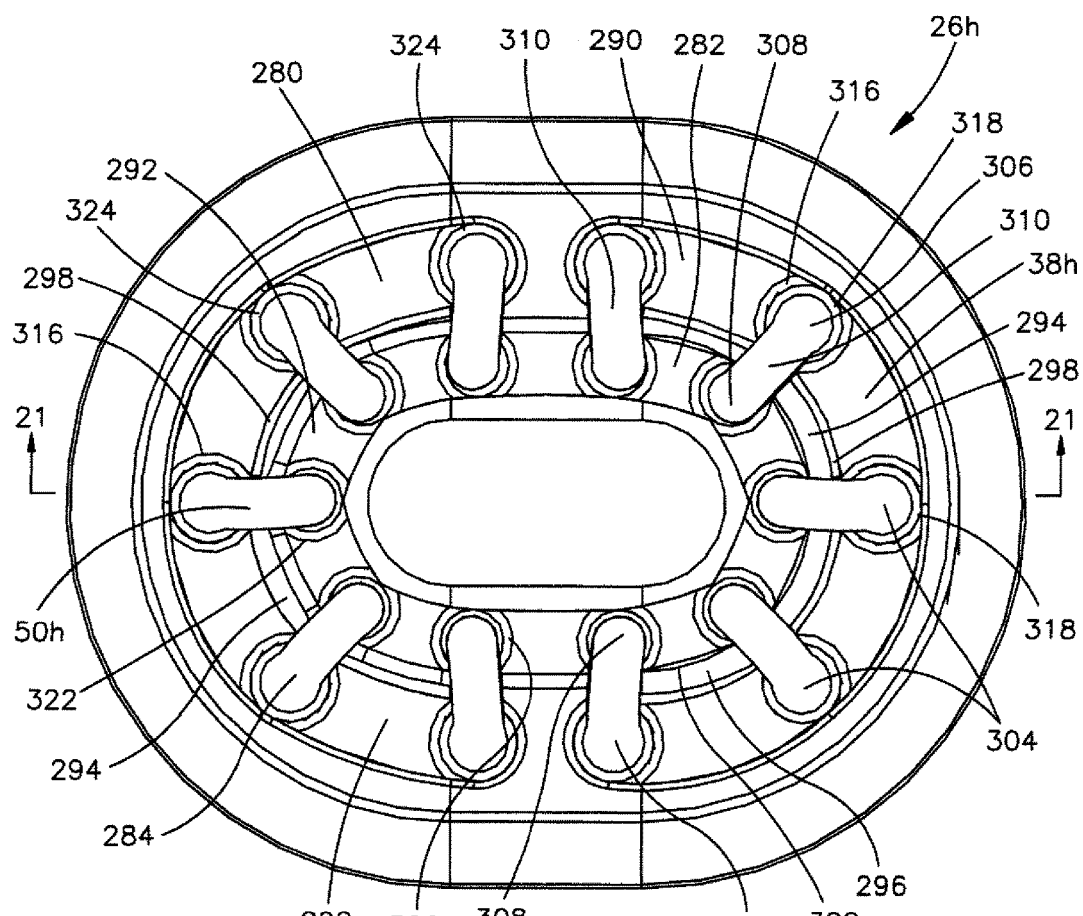
Figure 21:
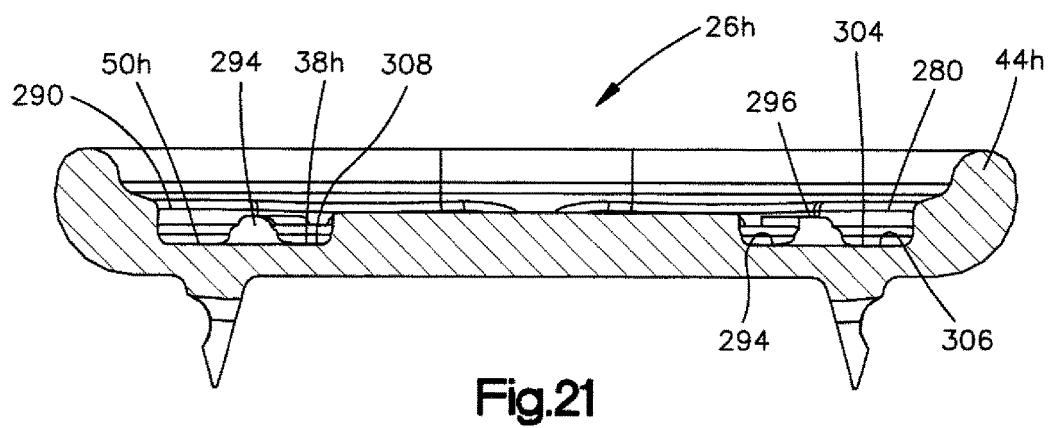

The embodiment of the invention illustrated in FIGS. 19-21 is generally similar to the embodiments of the invention illustrated in FIGS. 1-18. Therefore, similar components of the invention will be designated by similar numerals, the suffix letter "h" being added to the numerals of FIGS. 19-21 to avoid confusion.

A lower plate 26h (FIGS. 19-21) is used in an artificial disc similar to the artificial disc 10 of FIG. 1. The lower plate 26h has an inner side 38h which faces away from a lower vertebra, corresponding to the vertebra 14 of FIG. 1, and is fixedly connected to a resilient core, corresponding to the resilient core 20 of FIG. 1. An array 50h of recesses is formed in the inner side 38h of the lower plate 26h. The array 50h of recesses includes a first set of recesses 280, a second recesses 282 and a third set of recesses 284. Although the plate 26h is described as having three sets of recesses, it is contemplated that the plate may include any desired number of sets of recesses.

The first set of recesses 280 includes two U-shaped recesses 290. The recesses 290 are generally concentric with the peripheral rim 44h of the lower plate 26h. The second set of recesses 282 includes a recess 292 concentric with the recesses 290 and the peripheral rim 44h. It is contemplated that the recesses 290, 292 and the peripheral rim 44h may have any desired shape. Furthermore, the plate 26h may have any desired number of recesses 290, 292 even though the plate is shown as having two recesses 290 and one recess 292. It is also contemplated that the recesses 290 may form one recess that is concentric with the recess 292 and the peripheral rim 44h.

The recesses 290 and 292 are at least partially defined by U-shaped projections 294 extending between the recesses 290 and the recess 292. The projections 294 have U-shaped generally planar upper surfaces 296. A first continuous arcuate outer side surfaces 298 extends from a bottom of the recess 292 to the upper surface 296. A second arcuate outer side surface 300 extends from a bottom of the recess 292 to the upper surface 296. The continuous arcuate outer side surfaces 298, 300 have a convex configuration.

The third set of recesses 284 includes a plurality of recesses 304 extending generally transverse to the recesses 290, 292. The recesses 304 extend generally perpendicular to the recesses 290, 292. However, the recesses 304 may extend in any desired direction that is transverse to the recesses 290, 292. The recesses 304 intersect the recesses 290, 292. Although ten equally spaced recesses 304 are shown, it is contemplated that the plate 26h may have any desired number of recesses 304 spaced apart in any desired manner.

The recesses 290 have a depth less than the depth of the recess and 292. The recess 292 has a depth less than a depth of the recesses 304. It is contemplated that the recesses 290, 292 and 304 may have any desired depth. The recesses 290, 292 and 304 may all have different depths or the same depth if desired.

Each of the recesses 304 has a first semi-circular shaped longitudinal end 306 (as viewed in FIG. 20) and a second semi-circular longitudinal end 308. The first end 306 is located adjacent the recess 290 and the second end 308 is located adjacent the recess 292. A generally linearly extending central portion 310 extends between the first and second ends 306, 308.

The first end 306 is at least partially defined by an arcuate surface 316. The arcuate surface 316 has a generally convex shape and extends from the bottom of the recess 290 to a concave arcuate surface 318. The concave arcuate surface 318 extends from the convex arcuate surface 316 to a bottom of the recesses 304.

The second end 308 of each of the recesses 304 is at least partially defined by an arcuate surface 322. The arcuate surface 322 has a generally convex shape and extends from the bottom of the recess 292 to a concave arcuate surface 324. The concave arcuate surface 324 extends from the convex arcuate surface 322 to a bottom of the recesses 304.

The arcuate surfaces 298, 300, 316, 318, 322, 324, and the recesses 290, 292, 304 have continuously curving cross-sectional configurations. The arcuate surfaces 298, 300, 316, 318, 322, 324, and the recesses 290, 292, 304 are free of discontinuities. Therefore, there are no stress inducing corners in the arcuate surfaces 298, 300, 316, 318, 322, 324, and the recesses 290, 292, 304.

CONCLUSION

In view of the foregoing description, it is apparent that the present invention provides a new and improved artificial disc 10 which is utilized to replace a damaged spinal disc in a spinal column 16. The artificial disc 10 includes a resilient core 20 which is disposed between first and second plates 24 and 26. The first plate 24 has an outer side which is engageable with a first vertebra 12 of the spinal column 16 and an inner side. The second plate 26 has an outer side 40 which is engageable with a second vertebra 14 of the spinal column and an inner side 38.

In accordance with one of the features of the invention, the inner side of at least one of the plates 24 or 26 has an array 50 of recesses. The array 50 of recesses includes a plurality 54 of recesses 56 having the same configuration. Each of the recesses 56 of the plurality 54 of recesses have surfaces which are integrally formed as one piece with the one plate of the first and second plates.

If desired, the inner side of the other plate may also be provided with an array of recesses which may be formed in the same general matter and have the same general configuration as the recesses formed in the one plate. If desired, each of the recesses of the plurality of recesses in either one of the plates may have a rim portion formed by a polygonal array of interconnected rim sections.

In accordance with another of the features of the present invention, each of the recesses of the 146, 150, and 154 may extend in at least one row 148, 152, 156. The plurality of recesses 146, 150, 154 may extend in a plurality of rows 148, 152, 156 that may extend generally parallel to each other. Arcuate surfaces 145 defining the recesses in a first row 148 of recesses 146 may form an undulating wave having an amplitude greater than an amplitude of an undulating wave formed by arcuate surfaces 147 in a second row 152 of recesses 150.

Furthermore, the plurality of recesses may include at least first and second concentric recesses 210, 212, 250, 290, 292. The concentric recesses 210, 212, 250, 290, 292 may be at least partially defined by arcuate surfaces extending between the concentric recesses. The plurality of recesses may include at least one recess 214, 260, 304 extending generally transverse to the concentric recesses. The at least one recess 214, 260, 304 extending generally transverse to the concentric recesses may extend generally perpendicular to the concentric recesses. Also, the at least one recess extending transverse to the concentric recesses may have a first semi-circular shaped longitudinal end 306 and a second semi-circular shaped longitudinal end 308. At least one of the first and second semi-circular shaped longitudinal ends 306, 308 may be defined by generally convex arcuate surface 316, 322 extending from a bottom of one of the concentric recesses to a concave arcuate surface 318, 324 extending from the convex arcuate surface to a bottom of the at least one recess extending transverse to the concentric recesses.

From the above description of the invention, those skilled in the art will perceive improvements, changes and modifications. Such improvements, changes and modifications are intended to be covered by the appended claims.

Having described the invention, the following is claimed:

1. An artificial disc to replace a damaged spinal disc in a spinal column, said artificial disc comprising:
    a first plate having an outer side engagable with a first vertebra of the spinal column and an inner side,
    a second plate having an outer side engagable with a second vertebra of the spinal column and an inner side, and
    a resilient core disposed between said first and second plates, said resilient core being fixedly bonded to said inner sides of said first and second plates by molding the resilient core to the first and second plates,
    said inner side of at least one of said first and second plates having an array of recesses which includes a plurality of recesses into which said resilient core is molded and extends,
    wherein each one of said recesses comprises a bottom portion having a polygonal configuration and being configured to be filled with and comprising molded resilient core material,
    wherein said plurality of recesses are integrally formed in the entire inner side of said at least one plate of said first and second plates and wherein each one of said recesses of said plurality of recesses has surfaces which are integrally formed as one piece with said at least one plate of said first and second plates,
    wherein the resilient core comprises a material that is configured to flow into each of one said recesses by heating and softening the material, and
    wherein the second plate comprises a peripheral flange that restricts transverse or sideways deflection of the resilient core.

2. An artificial disc as set forth in claim 1 wherein each one of said recesses of said plurality of recesses has a rim portion formed by a polygonal array of interconnected rim sections.

3. An artificial disc as set forth in claim 2 wherein each one of said interconnected rim sections has a linear central axis and an arcuate outer side surface as viewed in a plane extending perpendicular to the central axis of said one of said rim sections.

4. An artificial disc as set forth in claim 3 wherein said arcuate outer side surface of said one of each interconnected rim sections forms a portion of a first recess and a portion of a second recess which is adjacent to said first recess.

5. An artificial disc as set forth in claim 4 wherein said arcuate outer side surface of said one of each interconnected rim sections has a continuously curving configuration and is free of discontinuities.

6. An artificial disc as set forth in claim 1 wherein each of one said recesses of said plurality of recesses has a rim portion formed by a rectangular array of rim sections.

7. An artificial disc as set forth in claim 1 wherein each one of said recesses of said plurality of recesses includes an arcuate bottom surface which has a continuously curving cross sectional configuration and extends from a rim portion on a first side of each one of each recesses to rim portion on a second side of said one of said recesses.

8. An artificial disc as set forth in claim 7 wherein each one of said recesses of said plurality of recesses includes first and second minor bottom surfaces, each of said minor bottom surfaces extends from a rim portion of each one of said recesses to an edge portion of said arcuate bottom surface of each one of said recesses.

9. An artificial disc as set forth in claim 1 wherein one of said first and second plates has an inner side which bows in a direction toward one of the first and second vertebra which engages said one of said first and second plates, said array of recesses having a bowed configuration with the same center of curvature as said inner side of said one of said first and second plates.

10. An artificial disc as set forth in claim 1 wherein one of said first and second plates is formed from a plate having a thickness of 1 millimeter or less.

11. An artificial disc as set forth in claim 1 wherein the plurality of recesses extend in at least one row.

12. An artificial disc as set forth in claim 11 wherein the plurality of recesses extend in a plurality of rows.

13. An artificial disc as set forth in claim 12 wherein the plurality of rows of recesses extend generally parallel to each other.

* * * * *